US012142358B2

(12) United States Patent
Mura et al.

(10) Patent No.: US 12,142,358 B2
(45) Date of Patent: Nov. 12, 2024

(54) DOCUMENT CREATION APPARATUS, METHOD, AND PROGRAM

(71) Applicants: OMRON Corporation, Kyoto (JP); OMRON HEALTHCARE CO., LTD., Muko (JP)

(72) Inventors: Seitaro Mura, Kyoto (JP); Hiroshi Usui, Kyoto (JP); Hirotaka Wada, Kyoto (JP)

(73) Assignees: OMRON Corporation, Kyoto (JP); OMRON HEALTHCARE CO., LTD., Kyoto (JP)

( * ) Notice: Subject to any disclaimer, the term of this patent is extended or adjusted under 35 U.S.C. 154(b) by 457 days.

(21) Appl. No.: 17/291,811

(22) PCT Filed: Oct. 16, 2019

(86) PCT No.: PCT/JP2019/040697
§ 371 (c)(1),
(2) Date: May 6, 2021

(87) PCT Pub. No.: WO2020/105324
PCT Pub. Date: May 28, 2020

(65) Prior Publication Data
US 2021/0391047 A1 Dec. 16, 2021

(30) Foreign Application Priority Data
Nov. 22, 2018 (JP) ................. 2018-219561

(51) Int. Cl.
G16H 15/00 (2018.01)
G16H 10/60 (2018.01)
(Continued)

(52) U.S. Cl.
CPC ............. *G16H 15/00* (2018.01); *G16H 10/60* (2018.01); *G16H 20/70* (2018.01); *G16H 50/30* (2018.01)

(58) Field of Classification Search
CPC ........ G16H 15/00; G16H 10/60; G16H 20/70; G16H 50/30; G16H 10/20; G16H 40/20
(Continued)

(56) References Cited

U.S. PATENT DOCUMENTS 7,792,783 B2 * 9/2010 Friedlander ............ G06Q 40/08
707/602
10,832,802 B2 * 11/2020 Barker .................. G06F 16/285
(Continued)

FOREIGN PATENT DOCUMENTS

JP 2002-056281 A 2/2002
JP 2010-277574 A 12/2010
(Continued)

OTHER PUBLICATIONS

International Search Report ("ISR") of the international application PCT/JP2019/040697 mailed on Jan. 14, 2020.
(Continued)

*Primary Examiner* — Hicham Skhoun
(74) *Attorney, Agent, or Firm* — METROLEX IP LAW GROUP, PLLC; Robert L. Scott, Esq.

(57) ABSTRACT

A document creation apparatus includes a first unit that acquires health data indicating a user health condition, a second unit that acquires at least one of consciousness data indicating user health consciousness, environment data indicating an environment related to user health, or knowledge data indicating a knowledge level related to the user health, a determination unit that determines a type of the user health based on a position of a point corresponding to the data acquired by the first unit and the second unit in a space (Continued)

spanned by bases, the bases being a vector having the health data, and at least one vector of a vector having the consciousness data, a vector having the environment data, or a vector having the knowledge data, and a creation unit that creates document data for a document to be presented to the user according to the type.

18 Claims, 25 Drawing Sheets

(51) Int. Cl.
    *G16H 20/70*     (2018.01)
    *G16H 50/30*     (2018.01)

(58) Field of Classification Search
    USPC .......................................................... 707/608
    See application file for complete search history.

(56) References Cited

U.S. PATENT DOCUMENTS

| | | | | |
|---|---|---|---|---|
| 2003/0140044 A1* | 7/2003 | Mok | ...................... | G16H 30/20 |
| 2003/0191669 A1* | 10/2003 | Fitzgerald | .............. | G16H 70/20 |
| | | | | 707/999.1 |
| 2003/0233250 A1* | 12/2003 | Joffe | ...................... | G16H 15/00 |
| | | | | 705/2 |
| 2004/0122704 A1* | 6/2004 | Sabol | ...................... | G07C 9/37 |
| | | | | 706/45 |
| 2005/0228692 A1* | 10/2005 | Hodgdon | ................ | G16H 10/40 |
| | | | | 705/2 |
| 2007/0118399 A1* | 5/2007 | Avinash | ................. | G16H 40/20 |
| | | | | 705/2 |
| 2008/0059242 A1* | 3/2008 | Stanford | ................ | G16H 10/60 |
| | | | | 707/999.107 |
| 2009/0150438 A1* | 6/2009 | Markisohn | ............. | G16H 10/60 |
| 2009/0228304 A1* | 9/2009 | Ciarniello | ............. | G16H 10/60 |
| | | | | 705/2 |
| 2010/0042440 A1* | 2/2010 | Joao | ....................... | G06Q 10/10 |
| | | | | 705/2 |
| 2010/0076786 A1* | 3/2010 | Dalton | ................... | G16H 10/60 |
| | | | | 707/E17.06 |
| 2011/0066451 A1* | 3/2011 | Jang | ....................... | G16H 15/00 |
| | | | | 707/E17.046 |
| 2013/0030260 A1* | 1/2013 | Hale | ...................... | G16H 50/30 |
| | | | | 600/301 |
| 2015/0106020 A1* | 4/2015 | Chung | ................... | G16H 40/67 |
| | | | | 702/19 |
| 2015/0347599 A1* | 12/2015 | McMains | .......... | G06F 16/24522 |
| | | | | 707/723 |
| 2016/0250751 A1* | 9/2016 | Martinson | ............. | G16H 10/60 |
| | | | | 700/253 |
| 2019/0189253 A1* | 6/2019 | Kartoun | ................. | G16H 50/70 |
| 2019/0221320 A1* | 7/2019 | Amini | .................... | G06Q 10/10 |
| 2019/0287661 A1* | 9/2019 | Nobre | .................... | G16H 40/63 |
| 2020/0111578 A1* | 4/2020 | Koblick | ................. | G16H 80/00 |

FOREIGN PATENT DOCUMENTS

| | | |
|---|---|---|
| JP | 2015-069531 A | 4/2015 |
| JP | 2018-124836 A | 8/2018 |

OTHER PUBLICATIONS

Written Opinion ("WO") of the international application PCT/JP2019/040697 mailed on Jan. 14, 2020.

Extended European search report (EESR) issued on Jul. 18, 2022 in a counterpart European patent application.

English translation of an International Preliminary Report on Patentability (IPRP) of the international application PCT/JP2019/040697 mailed on Jun. 3, 2021.

\* cited by examiner

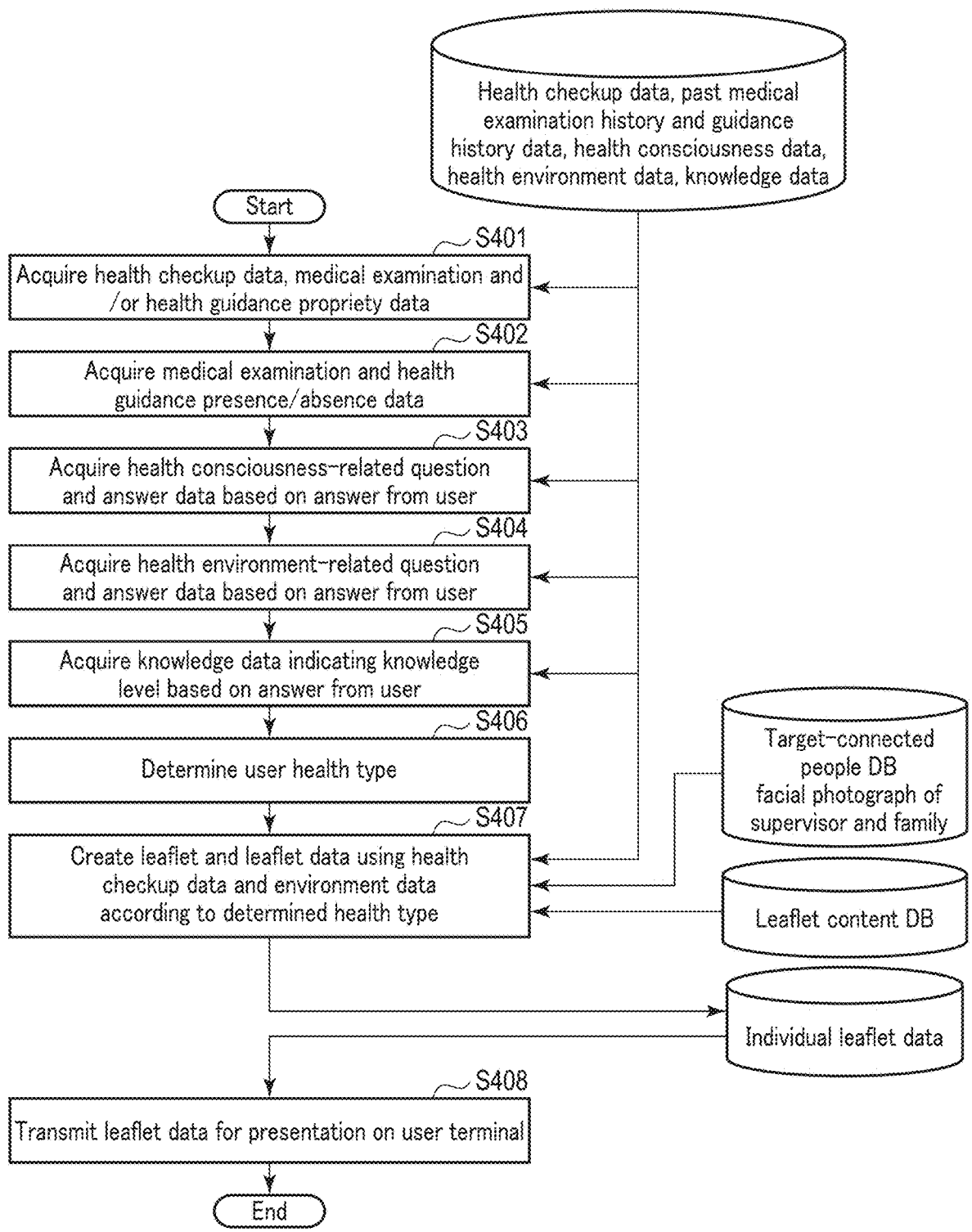
F I G. 4

| | | Presence/absence of health guidance and medical examination of last year | |
|---|---|---|---|
| | | Not conducted | Conducted |
| Medical examination recommendation | Severe | (4) Bad health checkup value and giving up Lowest health priority | (5) Has had prior medical examination(s) but result(s) was/were bad |
| Health guidance | Repeater | (2) Caught many times but never had medical examination | (3) Had medical examination but to no effect and abnormal values re-appeared |
| | Attention required / First time | (1) Person caught in health checkup first time but without knowledge and interest | |

FIG. 7C

| | Title | Content | | |
|---|---|---|---|---|
| | | FB of health checkup result | Presentation of expected behavior | Story |
| Severe and conducted (5) | Encouragement and value appeal "effect of continuation" | Inform severity by individual health checkup result | Please do first | Good story |
| Attention required and conducted | Repeater (3) | Encouragement and value appeal "effect of continuation" | | | |
| | First time | | | | |
| Severe and not conducted (4) | Attention and risk presentation "cerebral cardiovascular event" | | Please continue | Bad story |
| Attention required and not conducted | Repeater (2) | Attention and risk presentation "diet is restricted + change in body shape" | | | |
| | First time (1) | Attention and risk presentation "diet is restricted" | | | |

+

| | Repeater (3) | Severe and conducted (5) | First time | Repeater (2) | Severe and not conducted (4) |
|---|---|---|---|---|---|
| Expressions of people connected to targets displayed in leaflet change depending on type. | Expressionless | Expressionless | Sadness | Dislike | Anger |

FIG. 8

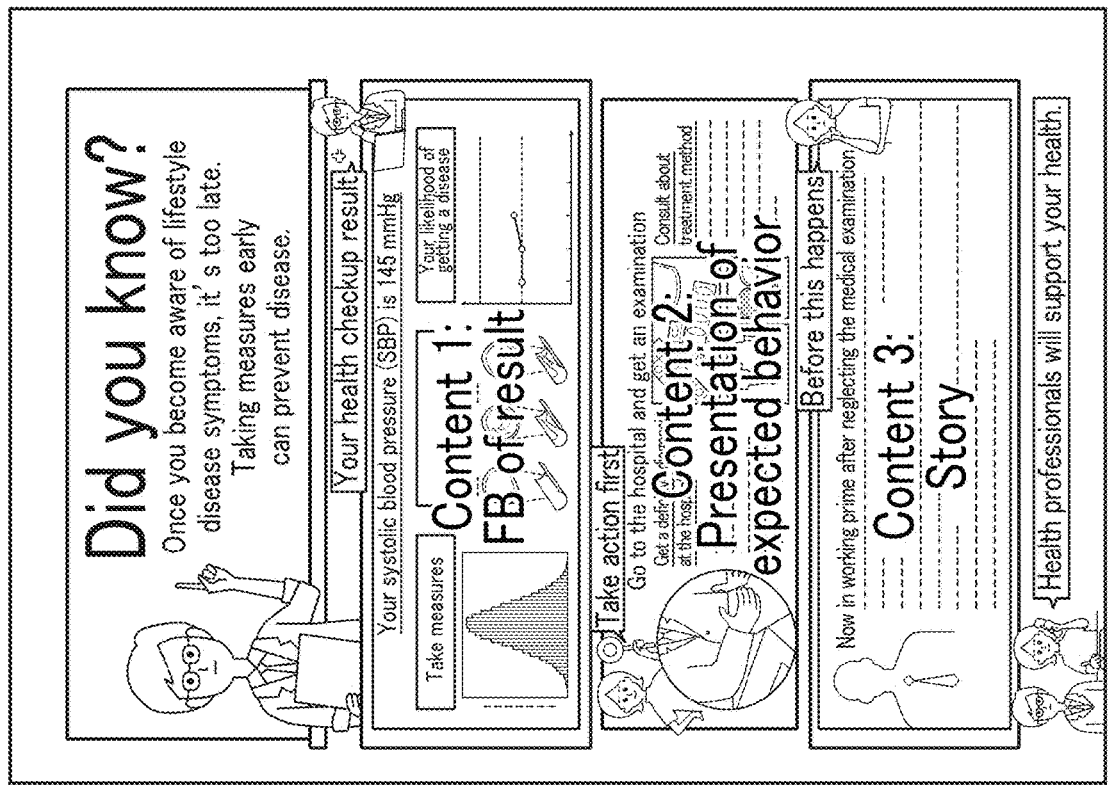
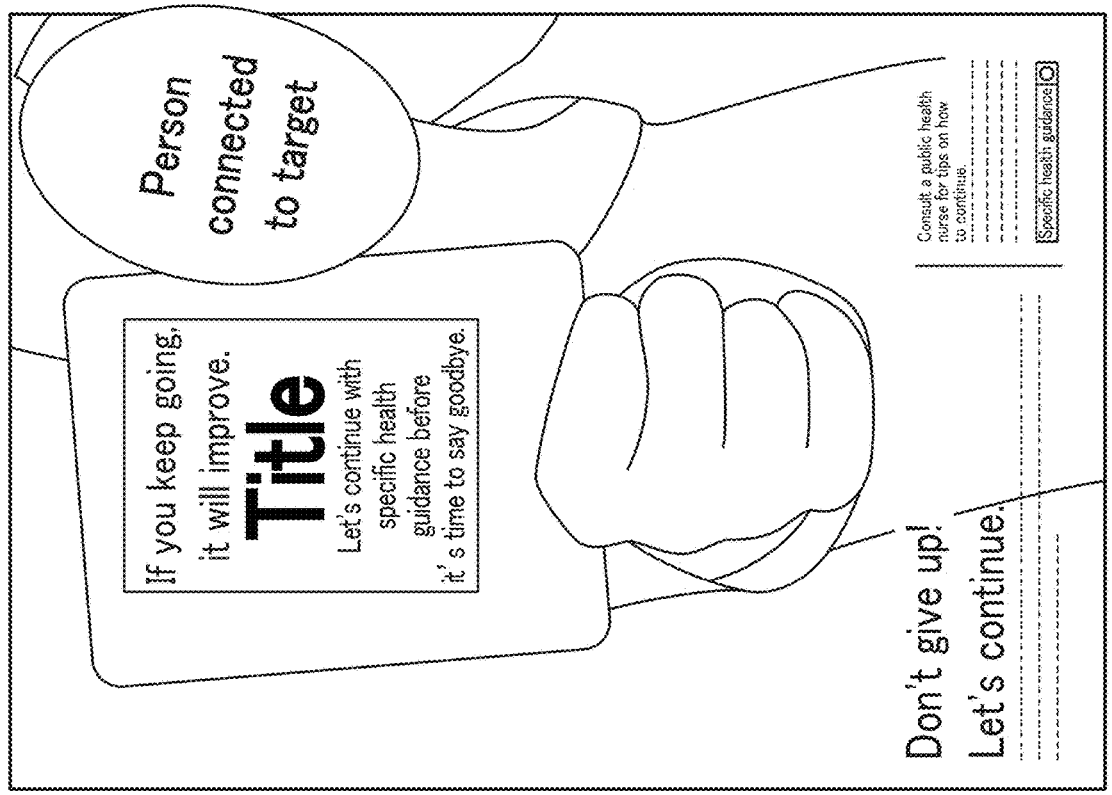
FIG. 9

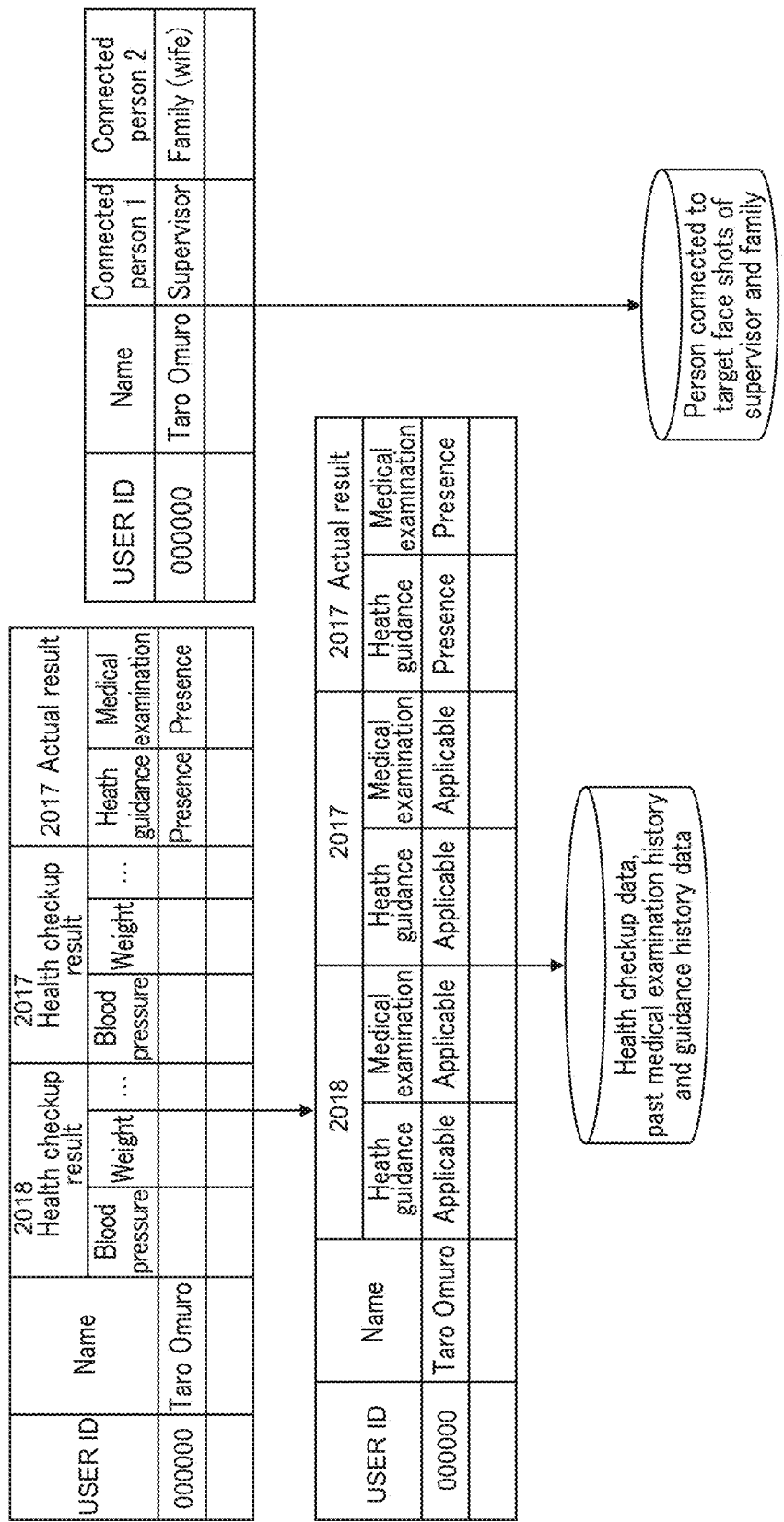
F I G. 10

| Classification | Content | Explanation |
|---|---|---|
| (1) | Get health guidance before you can't eat what you like. | Attention and risk (familiar content) |
| (2) | Your body is screaming. Diabetes, stroke, high blood pressure | Attention and risk (change in body shape) |
| (3) | Continue to receive specific health guidance! | Encouragement (continuity leads to effect) |
| (4) | This is the final warning. "Diabetes" "myocardial infarction" "arteriosclerosis" | Attention and risk (disease name, severe) |
| (5) | Never give up. Health professionals will support you | Value appeal (professional support) |

FIG. 12

| Classification | Story |
| --- | --- |
| | Content |
| (1)(2)(4) | Get a definitive diagnosis at the hospital! A health checkup result alone cannot inform you of your true health. Get a doctor's diagnosis first. Consult about treatment methods! Medicine is not the only cure. Talk to your doctor about the right diet and exercise balance. |
| (3)(5) | Continue to go to the hospital! It is important to have medical examinations continuously. By visiting the hospital to measure your physical condition every year, a detailed examination and ways to prevent lifestyle diseases can be proposed at an appropriate time. Consult about treatment methods! Treatment method is determined according to the age and health condition at that time, and the effect so far. By continuing, you will find a lifestyle habit improvement method that suits you. |

F I G. 14

| Classification | Content | Explanation |
|---|---|---|
| (1) | I'd been told I've had high blood pressure since I was young, but I haven't been treated for it. I didn't have any discernible symptoms and couldn't understand why I had to go to hospital when it didn't hurt or itch. | Present risks and disadvantages of continuing to avoid specific health guidance and medical examinations and neglect lifestyle diseases as a story. |
| (2) | Even though I was told to go to hospital, I continued to ignore my high blood pressure, saying "I can't go to the hospital regularly because I'm too busy" and "I can't continue". | |
| (4) | As a result, one day I suddenly suffered a stroke and collapsed, and experienced significant aftereffects. I'm so sorry to have burdened my family due to now needing long-term care. I constantly wish I had gone to hospital when I was young. | |
| (3) | I was caught in a health checkup every year. I knew that my eating habits were irregular, so I tried to be careful myself, but could deliver no results. I went to the hospital for the first time in the second year, but the next year, despite the doctor's guidance, an abnormal value again showed up in the health checkup. I was about to give up, but when I visited the hospital again, it turned out that although abnormal values were still there, some of them had improved, and I was taught exercise and dietary methods that specialize in the areas for which abnormal values were registered. Also, the amount of medicine was reduced from the previous year. | Present advantages obtained by continuing lifestyle improvement through specific health guidance and medical examination as a story. |
| (5) | As a result, I was able to continue even though fed up, and was able to lower the values for the next year's health checkup. I'm really glad I continued working on it without giving up. | |

F I G. 15

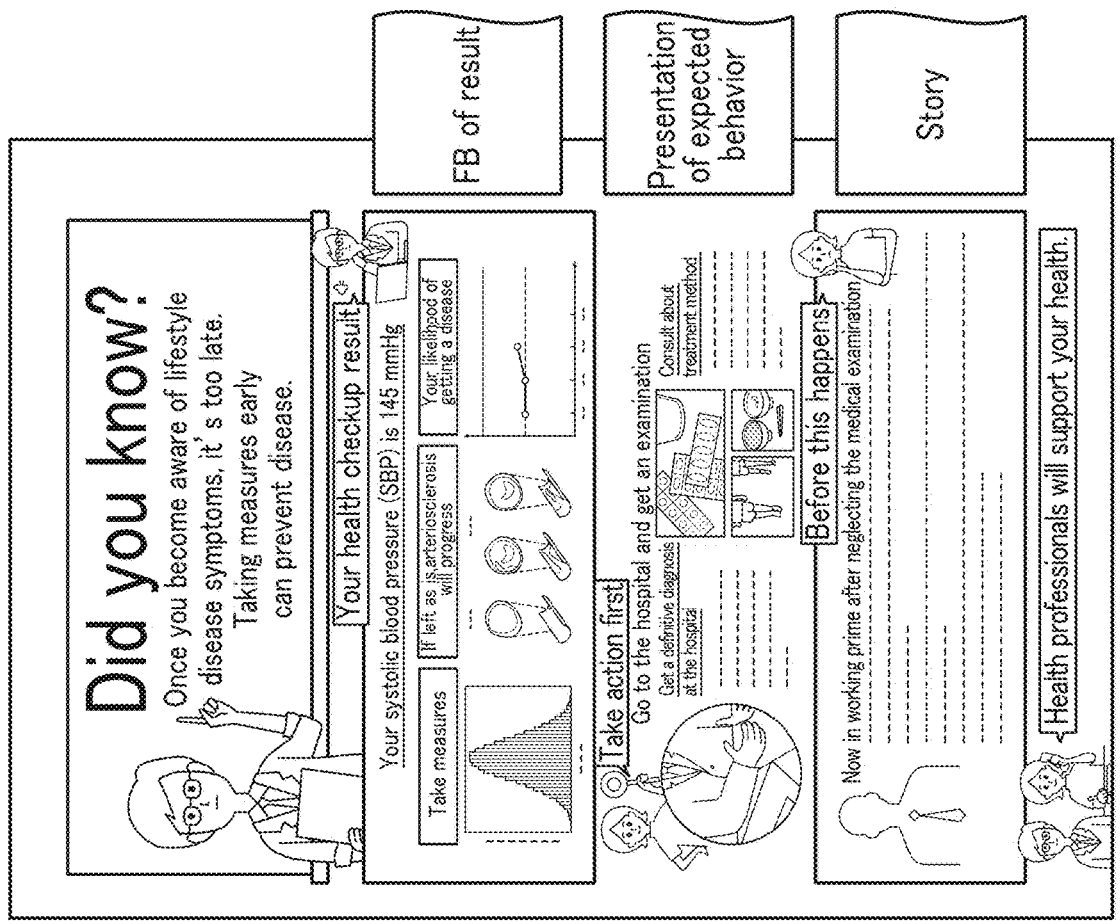
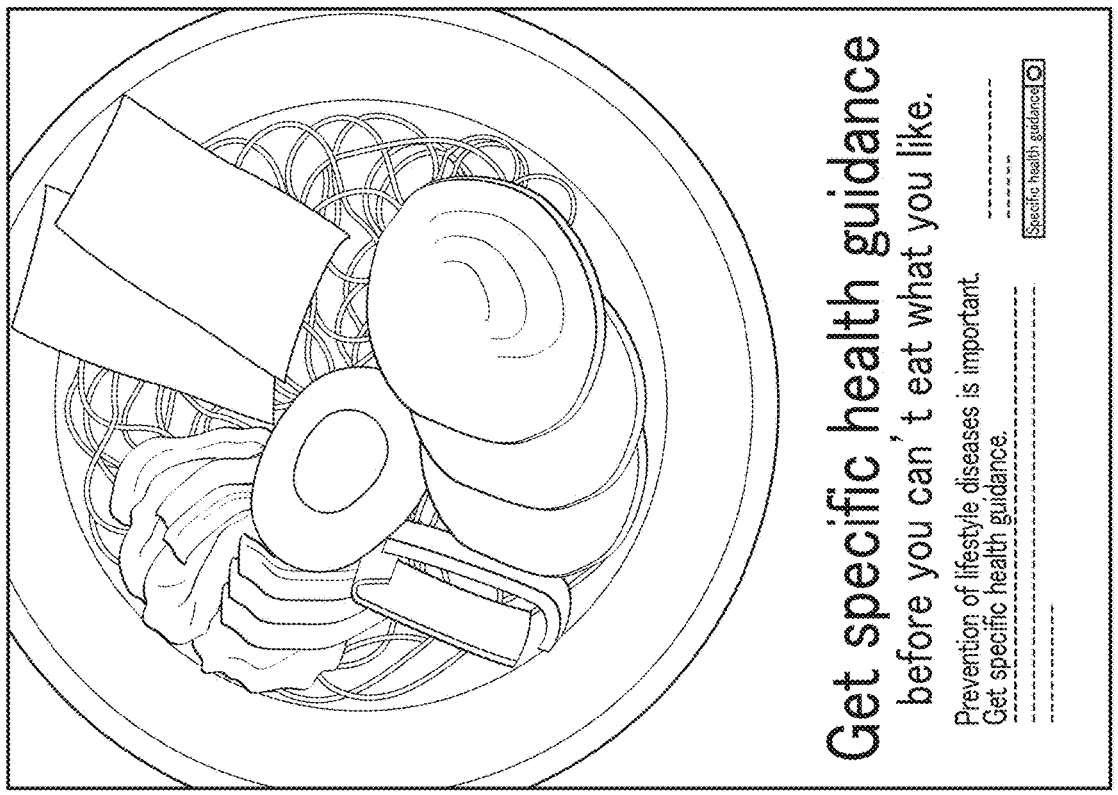
FIG. 18

| Item | Outline | Design intention |
|---|---|---|
| Attention : Attention | Perceptual delight, inquisitive delight, changeability | To be picked up and read. Not to be mixed in with other handouts. |
| Relevance : Relevance | Familiarity, purpose-oriented, motivational connection | To have the target look upon lifestyle disease as their own problem |
| Confidence : Confidence | Desire for learning, confidence in success, opportunity for success | To first present examples of actions that can be taken and foster a sense of control over those actions. |

F I G. 20

| Design | | |
|---|---|---|
| A | R | C |
|  | ○ |  |
|  |  | ○ |
| ○ |  |  |

+

| | | | Content | | Story |
|---|---|---|---|---|---|
| | | | | FB of health checkup result | Presentation of expected behavior | |
| Conducted | Severe (5) | | Title | | | |
| | | Repeater (3) | Encouragement and value appeal | | | |
| | | First time | Encouragement and value appeal | | Inform severity by individual health checkup result | |
| | Attention required | | Attention and risk presentation | | | Good story |
| Not conducted | Severe (4) | Repeater (2) | Attention and risk presentation | | | |
| | | First time (1) | Attention and risk presentation | | | |
| | Attention required | | | | | Bad story |

| | Content | |
|---|---|---|
| | Please do first | |
| | Please continue | |

FIG. 21

| | | | Notification time | Notification distance | Notification frequency |
|---|---|---|---|---|---|
| Conducted | Severe (5) | | When health checkup result is notified | 1km | Once |
| | Repeater (3) | | When health checkup result is notified | 500m | Once |
| | Attention required | First time | | | |
| Not conducted | Severe (4) | | When health checkup result is notified / Before health guidance application deadline | 1km | Twice |
| | Repeater (2) | | When health checkup result is notified / Before health guidance application deadline | 500m | Twice |
| | Attention required | First time (1) | When health checkup result is notified / Before health guidance application deadline | 100m | Twice |

F I G. 22

DOCUMENT CREATION APPARATUS, METHOD, AND PROGRAM

CROSS REFERENCE

This is a U. S. national phase application under 35 USC § 371 of International Application PCT/JP2019/040697 (not published in English), filed Oct. 16, 2019.

FIELD

The present invention relates generally to a document creation apparatus, a method, and a program.

BACKGROUND

In recent years, more than a few people (referred to as users or targets) have been required to improve their lifestyles as a result of a medical check, etc. For example, the high possibility of a lifestyle disease in the future or an existing lifestyle disease may be pointed out to the user via a health checkup or health examination (hereinafter collectively referred to as a "health checkup") conducted by a workplace or an organization of municipality.

In such a case, the user may, for example, plan to change their daily life in order to improve their lifestyle by asking for expert guidance or using a specialized application, etc. This planning includes designing daily life, for example, to reduce the amount of food intake, change the types of food and drink consumed, and increase exercise time by reviewing the current lifestyle in accordance with symptoms of the identified disease.

In order to prevent both the onset and increase in severity of lifestyle diseases and maintain overall health, it is important to undergo a health checkup, and, depending on the result, receive guidance from a health counselor or undergo a medical examination by a doctor. For example, in order to prevent diseases caused by lifestyle, guidance from a health counselor or a medical examination by a doctor is considered very effective for maintaining user health. The lifestyle diseases are caused by the contents of meals, smoking habits, exercise habits, drinking habits, etc.

However, the fact that many users are unwilling to proactively seek health counselor guidance or a doctor's medical examination in response to the health checkup unless the result shows a serious disease, or one requiring an urgent response, is a frequent problem.

Patent Literature 1 discloses, in relation to health guidance or medical examination recommendation, a health checkup institution identification unit that identifies, based on a health checkup history of a user of a portable terminal, a health checkup implementing institution at which the user is recommended to undergo a health checkup; a notification necessity determination unit that determines whether or not the portable terminal exists within a predetermined range based on the identified health checkup implementing institution; and an apparatus that transmits a message to the portable terminal to recommend a health checkup at the identified health checkup implementing institution to the user when the portable terminal exists within the predetermined range based on the identified health checkup implementing institution.

CITATION LIST

Patent Literature

[Patent Literature 1] Japanese Patent Application. KOKAI Publication No. 2018-124835

SUMMARY

Technical Problem

The above-described conventional apparatus calculates a health checkup institution score indicating a priority of a health checkup institution introduced to a user of a portable terminal, stores the score for each item, and refers to a notification condition table to specify a notification condition when recommending a specific health checkup based on a target score calculated from a target score table.

As described above, in the conventional apparatus, the guidance is created by applying a score obtained by one-dimensionally compressing health checkup history information from the target score table into the notification condition table. Thus, even if conditions observed at a health checkup differ, if the final scores are the same, the same guidance is transmitted. Therefore, the conventional apparatus renders it difficult to accurately grasp a user health condition at the time of a health checkup and impossible to effectively make the user aware of their health condition.

Further, there are cases in which a user receiving a health checkup is determined to have a health condition requiring attention, recommended for health guidance, and determined to have a severe health condition for which a doctor's medical examination is recommended. The number of users not receiving health guidance and/or undergoing a doctor's medical examination despite recommendations is not insignificant.

The high possibility of a user not electing to consider proactively receiving health guidance and/or undergoing a doctor's medical examination solely on the basis of having these needs explained to them can be surmised.

The present invention has been made in view of the above circumstances, and an aspect thereof is to provide a document creation apparatus, a method, and a program capable of creating a document to effectively induce user awareness so that the user proactively receives health guidance and/or a medical examination.

Solution to Problem

In order to solve the above-described problem, the present disclosure adopts the following configurations.

That is, a document creation apparatus according to a first aspect of the present disclosure includes a first acquisition unit that acquires health data indicating a user health condition; a second acquisition unit that acquires at least one of consciousness data indicating the user health consciousness, environment data indicating an environment related to the user health, or knowledge data indicating a knowledge level related to the user health; a determination unit that determines a type of user health based on positions of points corresponding to data acquired. by the first acquisition unit and the second acquisition unit in a space spanned by one or more bases, wherein the one or more bases are one or more vectors having the health data as a value, and at least one vector of: one or more vectors having the consciousness data as a value, one or more vectors having the environment data as a value, or one or more vectors having the knowledge data as a value; and a creation unit that creates document data for a document to be presented to the user according to the type.

In the above configurations, the first acquisition unit acquires user health data, and the second acquisition unit acquires at least one of the consciousness data, the environment data, or the knowledge data. These data are, for example, one-dimensional data (i.e., scalar values), each having scalar values in a unique axis. These axes are represented by vectors unique to the respective data, and correspond to different vectors respectively for the health data, the consciousness data, the environment data, and the knowledge data. In a space spanned by these vectors, characteristics related to the user health differ depending on which range of the space the user data belongs to. Therefore, the type of the user health can be determined by the range to which the user data belongs. Then, the creation unit creates a document to be presented to the user in accordance with the determined type, thereby allowing the document creation apparatus to create a document in a format and/or content, etc. most suitable for the user, in which data on the user health is reflected.

For example, when the health data, the consciousness data, the environment data, and the knowledge data are acquired, in a four-dimensional space spanned by bases which are vectors corresponding to these four data, the determination unit determines the type of the user health depending on the location of a vector in the four-dimensional space, the vector being determined by a set of four data, i.e., the health data, the consciousness data, the environment data, and the knowledge data of the user. For example, if each axis corresponding to one vector is classified into two ranges (i.e., one threshold is set for each axis), the types are classified into $2^4=16$. Then, the determination unit determines to which of these 16 types the user belongs. A creation unit creates a document corresponding to the determined type to which the user belongs from among the 16 types.

Here, the document includes not only a document using a paper medium but also digital content displayed on a monitor of a personal computer or a smartphone. The document also includes not only characters and images but also moving images, sounds, etc.

Each of the health data, the consciousness data, the environment data, and the knowledge data may correspond to a plurality of vectors. For example, in the case of the health data, when a value for each diagnostic item of a health checkup is associated with one vector, a plurality of vectors are associated with the health data. Similarly, a plurality of vectors can be associated with each of the consciousness data, the environment data, and the knowledge data, and in this case, type determination is performed in a multidimensional space of five dimensions or more.

Therefore, according to the present disclosure, it is possible to create a document reflecting content, a format, etc. suitable for each user based on the user health data and at least one of the consciousness data, the environment data, or the knowledge data. As a result, according to the present disclosure, it is possible to provide an optimal document for each user, and thereby help improve the user health condition. Therefore, it is possible to create a document to effectively make the user, etc. aware of their health condition.

Furthermore, the document creation apparatus according to the first aspect of the present disclosure may be any apparatus capable of executing a program for acquiring user health data and at least one of consciousness data, environment data, or knowledge data, determining a type related to user health, and creating a document, and may take the form of, for example, a wearable device (e.g., a smartphone or a wristwatch-type wearable terminal) or a stationary device (e.g., a personal computer).

In a document creation apparatus according to a second aspect of the present disclosure, the determination unit calculates both of severity of the user from the health data and a sense of crisis of the user from the consciousness data, and the determination unit determines the type based on at least one of the severity or the sense of crisis.

In the above-described configuration, the determination unit uses as data both user health data and user consciousness data, calculates, from the health data, for example, the severity of an item (e.g., a disease) impairing user health, which is found from the data; calculates, from the consciousness data, the degree of user's sense of crisis for the item impairing the health, and determines the type based on the severity and the sense of crisis. The severity and the sense of crisis, both of which are calculated based on digitized values, are calculated according to the range in which the respective values lie. The severity is classified into, for example, three types: if the severity is less than a first value, the health condition is termed "normal"; if the severity is equal to or greater than the first value and less than a second value, the health condition is termed "attention required"; and if the severity is equal to or greater than the second value, the health condition is termed "dangerous". Similarly, one or more threshold values are set for the sense of crisis, and the user's sense of crisis is calculated according to the range in which the digitized sense of crisis lies. Then, the determination unit determines the user type depending on where in the plurality of ranges classified by the severity and the sense of crisis the user data lies.

Therefore, according to the document creation apparatus of the second aspect of the present disclosure, it is possible to determine the type related to user health by determining to which range in a two-dimensional space generated by the two indexes of user severity and sense of crisis the user data belongs.

In a document creation apparatus according to a third aspect the present disclosure, the determination unit determines whether to encourage the user to undergo a doctor's medical examination, recommend the user to receive health guidance, or neither the encouraging or the recommending according to the type, and the creation unit creates the document including content changed according to this determination result.

In the above-described configuration, the determination unit determines which of the three health conditions the user fits according to the type determined by the determination unit, and the creation unit changes the content in accordance with this determination result and creates the document according to the determination result. That is, according to the document creation apparatus of the third aspect of the present disclosure, it is possible to determine which of the three states (encouraging the user to visit a doctor (e.g., severe), recommending the user to receive health guidance (e.g., attention required), or neither of the above (e.g., normal)) the user fits based on the determined type, and create a document by changing the content of the document to be created by the creation unit according to this determination result (e.g., whether the user's disease is in a "severe" or "attention required" phase, or the user health condition is in a "normal" phase).

In a document creation apparatus according to a fourth aspect of the present disclosure, the determination unit digitizes the consciousness data according to an answer from the user to a question about user health consciousness, digitizes the environment data according to an answer from the user to at least one of the questions about user diet, user exercise, user sleep, a family medical history, or the smoking status of people around the user, and digitizes the knowledge data according to an answer from the user to a question about user health knowledge.

In the above-described configuration, the determination unit digitizes each of the consciousness data, the environment data, and the knowledge data acquired by the second acquisition unit according to an answer to a question to the user. The consciousness data is digitized by obtaining an answer to a question about health consciousness from the user. The environment data is digitized by obtaining, from the user, an answer to at least one of the questions about a user diet, user exercise, user sleep, a family medical history, or the smoking status of people around the user. The knowledge data is digitized by obtaining from the user an answer to a question about user health knowledge. For example, the answers to these questions are of a selection type, a score is assigned to each selectable option, scores of selected answers are integrated, and the determination unit digitizes the data with the value. When the type is determined, the user type can be determined depending on where the data is located in a space of at least two dimensions or more defined by a vector to which the health data corresponds and vectors to which the consciousness data, the environment data, and the knowledge data respectively correspond.

In addition, the environment data may be digitized for each of answers to a plurality of questions in a multidimensional manner. For example, the determination unit may use, for the type determination, a five-dimensional space spanned by vectors respectively corresponding to the daily number of user mealtimes, an amount of user exercise, a user sleeping time, a numerical value based on a family medical history (e.g., a value corresponding to a period of illness weighted based on a degree of consanguinity, etc.), and a value corresponding to a time during which a person around them is smoking and thus exposing the user to smoke.

A document creation apparatus according to a fifth aspect of the present disclosure further includes a priority determination unit that determines to adopt, from data included in the health data, data whose priority of presentation to the user is higher than a threshold value in a descending order of priority, and the creation unit creates the document using the adopted data.

In the above-described configuration, an example of a method for selecting data to be adopted by the creation unit for a document from among the health data acquired by the first acquisition unit is indicated. In this document creation apparatus according to the fifth aspect, a priority is assigned to each data among the data included in the health data, data having a priority higher than a threshold value is preferentially adopted, and a document is created using the preferentially adopted data. Therefore, according to the document creation apparatus of the fifth aspect, data to be presented to a user can be adopted from among the data included in the health data based on the priority, making it possible to present, to the user, content using data more useful to the user.

The priority and the threshold value may be changed for each user. For example, these priority and threshold value may be changed based on other data (e.g., the consciousness data of the user, the environment data of the user, and/or the knowledge data of the user). Specifically, for example, as the user consciousness data is higher and/or as the user knowledge data is higher, the threshold value is lowered to make it easier to create a document using large amounts of detailed health data. In addition, when it is determined whether or not there is a disease based on past user health checkup data, etc. and if a disease is present, a high priority may be assigned to data serving as a risk factor of the disease.

A document creation apparatus according to a sixth aspect of the present disclosure further includes generation unit that generates a new space in which the number of dimensions is reduced using a principal component analysis from a dimensional space having the number of dimensions corresponding to the number of vectors, and the determination unit determines the type based on one or more principal component vectors of the new space.

In the above-described configuration, the number of dimensions of the space used in determining the type related to the user health is reduced using the principal component analysis to generate a new space. For example, the document creation apparatus according to the sixth aspect can associate two components obtained by the principal component analysis with vectors, respectively, and determine a type related to the user health in a two-dimensional space spanned by these vectors. According to this method, it is possible to adopt components having high contribution rates and associate these components respectively with vectors by the principal component analysis, and determine a type in a multi-dimensional space spanned by these vectors. For example, a threshold value is set by the principal component analysis, and type determination is performed in a multi-dimensional space (which may also include one dimension) in which only principal components corresponding to eigenvalues equal to or greater than the threshold value are adopted and corresponding vectors used as bases, without adopting principal components corresponding to eigenvalues lower than the threshold value. Through this type determination, the type determination can be performed based on a component estimated to have a large influence in the determination. As a result, it is possible to reduce the number of dimensions of the space by using only effective components for determination and thereby efficiently perform the type determination.

In a document creation apparatus according to a seventh aspect of the present disclosure, the creation unit creates at least one of: title data indicating a title of the document, feedback data to the user with respect to a health checkup result included in health data of the user, behavior data indicating a behavior expected of the user corresponding to the type, story data indicating a story according to at least one of an advantage and a disadvantage indicated by the behavior data, expression data included in the environment data and indicating an expression according to the type, design data indicating an arrangement of content of the document, layout data of content included in the document according to the type, or image data of a diagram and a photograph, wherein content of the data is changed for each of the types, and uses the created data as content included in the document.

As the above-described configuration includes a case where the creation unit generates data including a title of a document, feedback of a health checkup result to a user, an expected user behavior, a story according to an advantage and/or a disadvantage due to this behavior, a photograph indicating an expression, an arrangement of the document, a document content layout, and a diagram and a photograph according to the user type, a document to be created can be changed to have content suitable for the user. Therefore, the document creation apparatus according to this aspect can create an optimum document for each user.

In a document creation apparatus according to an eighth aspect of the present disclosure, the creation unit creates the title data, the feedback data, the behavior data, the story data, the expression data, and the design data according to at least one of the type or the knowledge data.

In the above-described configuration, since the creation unit creates the title data, the feedback data, the behavior data, the story data, the expression data, and the design data based on the determined user type and/or the user knowledge data, it is possible to create a document corresponding to the user type and/or user health knowledge level. As a result, for example, detailed and accurate data is created if the user requires a detailed explanation and/or has a high health knowledge level, and simple and conceptual data is created if this is not the case. In the former case, it is considered that an explanation and a diagram are created with content capable of providing the user with accurate data such as numerical values, and in the latter case, a diagram of, for example, numerical values is minimized to create content which can be intuitively understood.

In a document creation apparatus according to a ninth aspect of the present disclosure, the creation unit creates data including a display format and a text corresponding to the type of the user as the feedback data.

In the above-described configuration, the creation unit creates data including a display format and a text suitable for a user as feedback data to the user. For example, the creation unit selects a display format and a text according to a user type and/or knowledge level and displays the feedback data. For example, the creation unit displays either a distribution graph of health checkup values and the number of persons, or a graph indicating history data of health checkup values from past to present, according to the user. Alternatively, the creation unit may provide a detailed explanation about a health condition corresponding to a health checkup value of a user or display only the most important content. The display format shows several ways of how the content may be displayed, e.g., itemizing, giving detailed notes about terms, whether to use technical terms for comments, whether to use more illustrations, etc.

In a document creation apparatus according to a tenth aspect of the present disclosure, the creation unit creates, as the story data, either a story representing an advantage included in the behavior data, or a story representing a disadvantage when the type includes content caused by a bad user habit, and creates data including layout data of content included in the document and image data of a diagram and a photograph, according to the type.

In the above-described configuration, since the creation unit creates story data representing either an advantage included in behavior data or a disadvantage caused by a bad user habit, representing the advantage of the behavior data expected of the user in accordance with the story, the user can understand the effects to be gained by the behavior. Accordingly, since the user can understand in advance an advantage of the behavior data to be implemented, the user is motivated to implement this behavior. On the other hand, by representing the disadvantage caused by a bad user habit, the user can understand how their health condition deteriorates if they continue the bad habit. Therefore, the user can grasp the disadvantage stemming from their own habit, and thereby become motivated to improve their lifestyle in the future.

In addition, since the creation unit creates layout data for determining how to lay out text content according to type, a document displayed with a content layout suitable for the user type is created. In addition, since the creation unit also creates image data of a diagram and a photograph included in the document according to the type, it is possible to effectively highlight the content to the user and effectively make the user aware of their health condition.

In a document creation apparatus according to an eleventh aspect of the present disclosure, the second acquisition unit acquires portrait data of a person connected to the user, and the creation unit creates the expression data using the portrait data.

In the above-described configuration, since the second acquisition unit acquires portrait data connected to a user, the creation unit can create expression data corresponding to the user type by using the portrait data. As a result, since the expression of the person connected to the user is included in the document content, it can be expected that the user will pay more attention to the document.

Note that the "person connected to the user" includes not only someone they personally know, such as a family member, a relative, a friend, or an acquaintance, but a well-known person with whom they have no personal connection, such as an entertainer, an intellectual, and a celebrity. The connected person may also include fictional characters appearing in movies, cartoons, animations, etc. Further, the connected person may include not only a human but also an alien, an animal, a monster, a robot, etc.

A document creation apparatus according to a twelfth aspect of the present disclosure further includes a transmission unit that transmits the document data to a terminal capable of receiving the document data and displaying the document.

According to the above-described configuration, the transmission unit can transmit the document data created by the creation unit to another terminal. Since this terminal can receive the document data and display the document included in the data, the user can view content of the document displayed by the terminal. Therefore, even if the user is physically away from the document creation apparatus, s/he can still check the document content if carrying the terminal. In addition, the document data may include a moving image which, with appropriate settings, can be reproduced by the terminal.

A document creation apparatus according to a thirteenth aspect of the present disclosure further includes a presentation unit that presents content represented by the document data to the user.

In the above-described configuration, the document creation apparatus further includes a presentation unit which can present content represented by created document data to a user. Therefore, the user can confirm the document content presented by the document creation apparatus.

A document creation apparatus according to a further aspect includes: a first acquisition unit that acquires health data indicating a health condition of a user; a second acquisition unit that acquires at least one of consciousness data indicating user health consciousness, environment data indicating an environment related to the user health, or knowledge data indicating a knowledge level related to the user health; and a creation unit that creates data including suitable health-related content for the user to be notified to that user based on the health data and at least one of the consciousness data, the environment data, or the knowledge data.

In the above configuration, the first acquisition unit acquires user health data, and the second acquisition unit acquires at least one of the consciousness data, the environment data, or the knowledge data. Such data is, for example, one-dimensional data (i.e., scalar values), each having a unique axis scalar value. The creation unit creates data including content to be notified to the user based on the health data and at least one data of the consciousness data, the environment data, or the knowledge data. For example, the creation unit can set one or more characteristic threshold values for each of these data, associate content related to the user health with each range determined by these threshold values, and determine content to be created depending on the range to which the user data belongs. Then, the creation unit creates content to be notified to the user based on the determined content. Accordingly, it is possible to create a document having the created data in a format and/or content, etc. most suitable for the user that reflects data on the user health. The one-dimensional data may take the form of a so-called "binary value" indicating whether or not the data belongs to a certain range or corresponds to a certain condition or not.

Thus, according to the present disclosure of this aspect, it is possible to create a document reflecting content, a format, etc. suitable for each user based on the health data of the user and at least one of the consciousness data of the user, the environment data of the user, or the knowledge data of the user. As a result, according to the present disclosure, it is possible to provide an optimal document for each user, and thereby help improve the user health condition. Therefore, it is possible to create a document to effectively make the user, etc. aware of their health condition.

ADVANTAGEOUS EFFECTS OF INVENTION

According to the present invention, in one aspect, it is possible to provide a document creation apparatus, a method, and a program capable of creating a document to effectively make the user aware of the need to proactively receive health guidance and/or undergo a medical examination.

BRIEF DESCRIPTION OF THE DRAWINGS

FIG. 4 is a flowchart schematically showing an example of a processing procedure related to the document creation apparatus according to the embodiment.

FIG. 7C is a table showing an example of types related to the user health based on the two axes of severity and sense of crisis.

FIG. 8 is a table showing an example of content to be displayed on a leaflet for each health-related type.

FIG. 9 is a diagram showing a specific example of a draft leaflet created based on the table of FIG. 8.

FIG. 10 is a diagram showing an example of health checkup data, and data indicating propriety of a medical examination and health guidance and whether or not a medical examination has been undergone and health guidance received, acquired in steps S401 and S402 of FIG. 4.

FIG. 12 is a diagram showing sample leaflet content DB for determining a title in step S1101 of FIG. 11.

FIG. 14 is a diagram showing sample leaflet content DB for determining the presentation of an expected behavior in step S1103 of FIG. 11.

FIG. 15 is a diagram showing sample leaflet content DB for determining a story in step S1104 of FIG. 11.

FIG. 18 is a diagram showing an example of a leaflet in which leaflet units are integrated in step S1107 of FIG. 11.

FIG. 20 is a table showing an example of change content which sees the document creation unit of FIG. 3 change the content and a design of the leaflet for each type.

FIG. 21 is a table showing an example of the content of the design shown in FIG. 20 to be displayed on the leaflet for each type related to health in relation to the table shown in FIG. 8.

FIG. 22 is a table showing an example in which a user notification time, a notification distance, and a notification frequency are associated for each health type.

DETAILED DESCRIPTION

Hereinafter, an embodiment (hereinafter also referred to as "the present embodiment") according to one aspect of the present invention will be described based the drawings. In the following embodiments, portions denoted by the same numbers operate similarly, and any repetitive description will be omitted.

[Outline]

Figure 1:
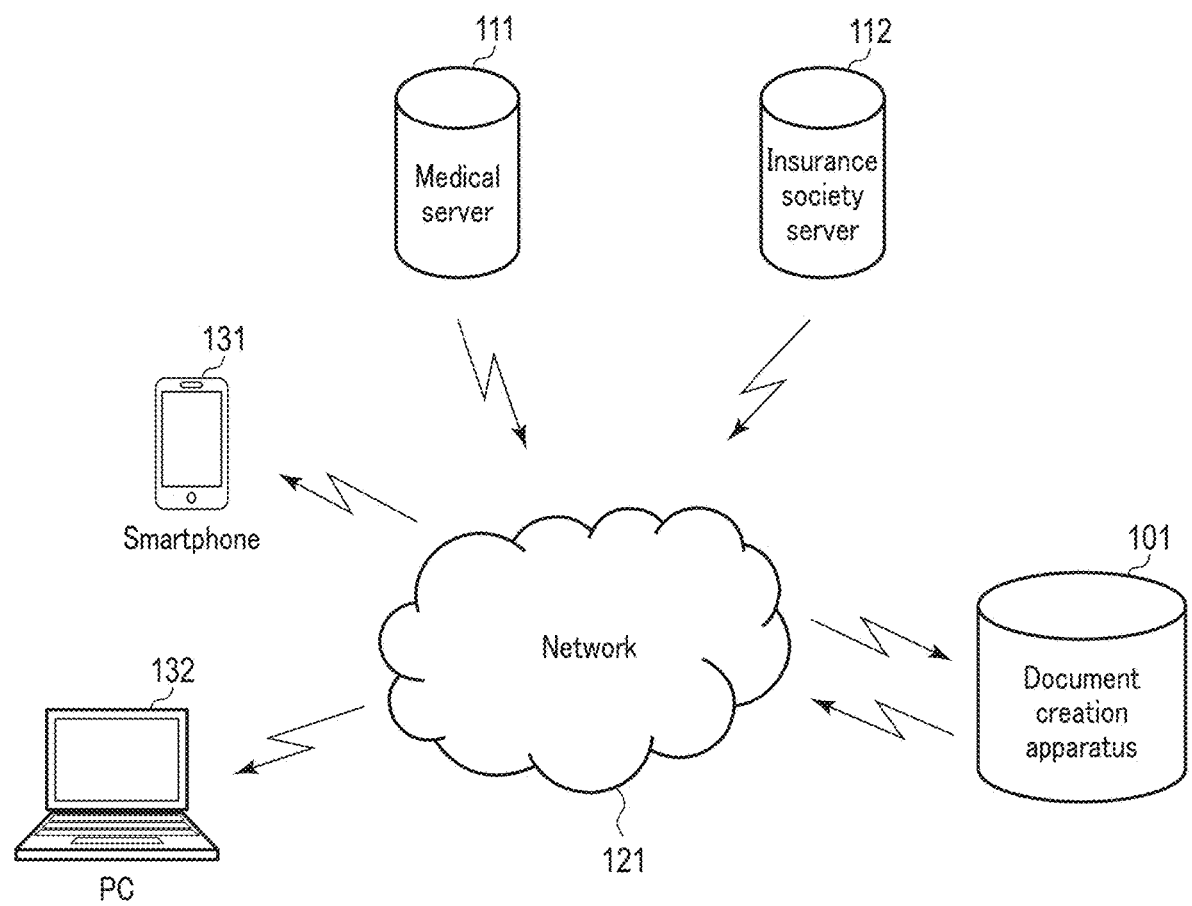
FIG. 1 is a diagram showing an outline of a system including a document creation apparatus (document creation server) according to an embodiment, a medical server, an insurance society server, a smartphone and a personal computer connected via a network.

First, an outline of a document creation apparatus according to the present invention will be described with reference to FIG. 1. FIG. 1 schematically shows a document creation apparatus (typically, a server) 101 according to an example of the outline, a medical server 111, an insurance society server 112, a smartphone 131, and a computer (PC) 132.

The document creation apparatus 101 receives, via a network 121, user medical data from the medical server 111, and user health guidance data and health checkup data from the insurance society server 112, and, for each user, creates health-related document data to be presented to the user. The document creation apparatus 101 transmits the created document data to the smartphone 131 and/or the computer 132 via the network. The document creation apparatus 101 may transmit the document data to a printer and print out accordingly.

The medical server 111 is a server that stores medical data of a hospital, and stores and updates medical data of users. It is assumed that the medical server 111 is a generic name for servers of a plurality of hospitals, and includes medical data stored by all those hospitals.

The insurance society server 112 is a server that stores insurance society data, which is data related to insurance societies, and stores and updates user health checkup data and health guidance data. It is assumed that. the insurance society server 112 is a generic name for servers of a plurality of insurance societies, and includes data stored by all those insurance societies.

The smartphone 131 and the computer 132 are capable of receiving document data from the document creation apparatus 101 and displaying and/or reproducing content indicated by the document data.

In addition, the document creation apparatus 101 acquires various data related to health of a user, determines a type related to the user health based on these data, and, based on this type, creates the document data for a document to be presented to the user. The document creation apparatus 101, for example, acquires medical data (included in the consciousness data of the invention) from the medical server 111, acquires health checkup data (corresponding to the health data of the invention), health guidance data (included in the consciousness data of the invention), question and answer data (corresponding to the environment data of the invention) about environment, and health knowledge data (corresponding to the knowledge data of the invention) indicating a user knowledge level from the insurance society server 112, determines the type related to the user health based on these data, and creates the document data based on this type. In addition, the consciousness data of the invention may be determined based on answer data (referred to as the "health consciousness-related question and answer data") of the user to a question about user health consciousness. The health consciousness data (corresponding to the consciousness data of the invention) of the user includes the medical data, health guidance data, and/or health consciousness-related question and answer data.

The medical data is medical examination propriety data indicating whether or not the user needs to be examined in a hospital, medical examination presence/absence data indicating whether or not a user who needs to be examined actually undergoes a medical examination, and may further include electronic medical record data when the user is examined in the hospital. By referring to the medical data, it is possible to determine whether or not a medical examination is undergone at a medical institution based on the degree of risk determined from health checkup data.

The health guidance data is health guidance propriety data indicating whether or not the user is applicable for health guidance, and health guidance presence/absence data which is data indicating whether or not the user receives the health guidance, and may further include data of health guidance content (the item of the health checkup data to which the health guidance corresponds, etc.). A standard of whether or not the health guidance is applicable to the user follows, for example, the standard of specific health guidance defined by the Ministry of Health, Labor and Welfare, but other standards may be adopted regardless as long as they are appropriately set.

The health checkup data is data for each health item examined when the user undergoes a health checkup. Although the items of the health checkup data differ depending on the health checkup, t is desirable that an item important for finding a disease is stored in the insurance society server 112 together with a priority. The health checkup data used by the document creation apparatus 101 may be one type (e.g., blood pressure value data).

The environment-related question and answer data is data concerning a question about a user health environment and an answer to the question, and takes the form of digitized data in this example. The environment-related question and answer data includes lifestyle data, e.g., user diet, user exercise, user sleep, favorite user food and drink, a family medical history, and a smoking status of people around the user, which are respectively digitized, the sum thereof including the user's environment-related question and answer data. A numerical value of the environment-related question and answer data is a numerical value of the degree to which something is good for user health; for example, an increase in this degree corresponding with an increased positive numerical value, and an increase in the degree to which something is bad leading to an increased negative numerical value. Other environment data may include face shots of family members and/or co-workers and work supervisors, which may be used to create a document.

The health knowledge data is, for example, question and answer data about knowledge, i.e., data of a question about user health knowledge and an answer to the question, and takes the form of digitized data in this example. The knowledge-related question and answer data includes questions and answers about various aspects of health knowledge, numerical values are assigned depending on the answers, and, for example, a sum of these numerical values includes the knowledge-related question and answer data. For example, the knowledge-related question and answer data is assigned a negative numerical value when the user has incorrect knowledge, zero value when the user does not have knowledge, and a positive numerical value when the user has correct knowledge. A numerical value having a larger absolute value is assigned for the more important knowledge related to one's life, a negative value is assigned in the case of erroneous recognition, and a positive value is given in the case of correct recognition.

The document creation apparatus 101 determines the user type from these data. The user type is calculated based on numerical values respectively indicated by the health checkup data, health guidance data, environment-related question and answer data, and knowledge-related question and answer data. One or more threshold values are set based on characteristics indicated by the respective data, and a range is set based on the threshold values. Since this range is set for all the data, if there are four categories of data, there are at least 16 ranges, and in this case, the 16 ranges correspond to the respective types.

The document creation apparatus 101 may determine a type for a certain disease, and may, for example, determine a user type for high-blood pressure. In this case, the health checkup data, health guidance data, environment-related question and answer data, and knowledge-related question and answer data all include only data on blood pressure. In addition, the document creation apparatus 101 may determine a type concerning a plurality of diseases. In this case, regarding these diseases, health checkup data, health guidance data, environment-related question and answer data, and knowledge-related question and answer data may be used to determine the user type. In this case, it is desirable to weight these four respective data sources for each disease to obtain a numerical value.

As described above, according to the document creation apparatus 101 of the present embodiment, characteristics related to the user health differ depending on the range among several determined by the health checkup data, health guidance data (and/or health consciousness-related question and answer data), environment-related question and answer data, and knowledge-related question and answer data to which the user data belongs, and a user health-related type can be determined depending on the range to which the user data belongs. Then, the document creation apparatus 101 can create a document to be presented to the user according to the determined type. Since the created document corresponds to the determined type, the document creation apparatus 101 can create the document in a format and/or content, etc, most suitable for the user and that reflects user health-related data.

CONFIGURATION EXAMPLE (Hardware Configuration)
<Document Creation Apparatus>

Next, an example of a hardware configuration of the document creation apparatus 101 according to the present embodiment will be described with reference to FIG. 2.

Figure 2:
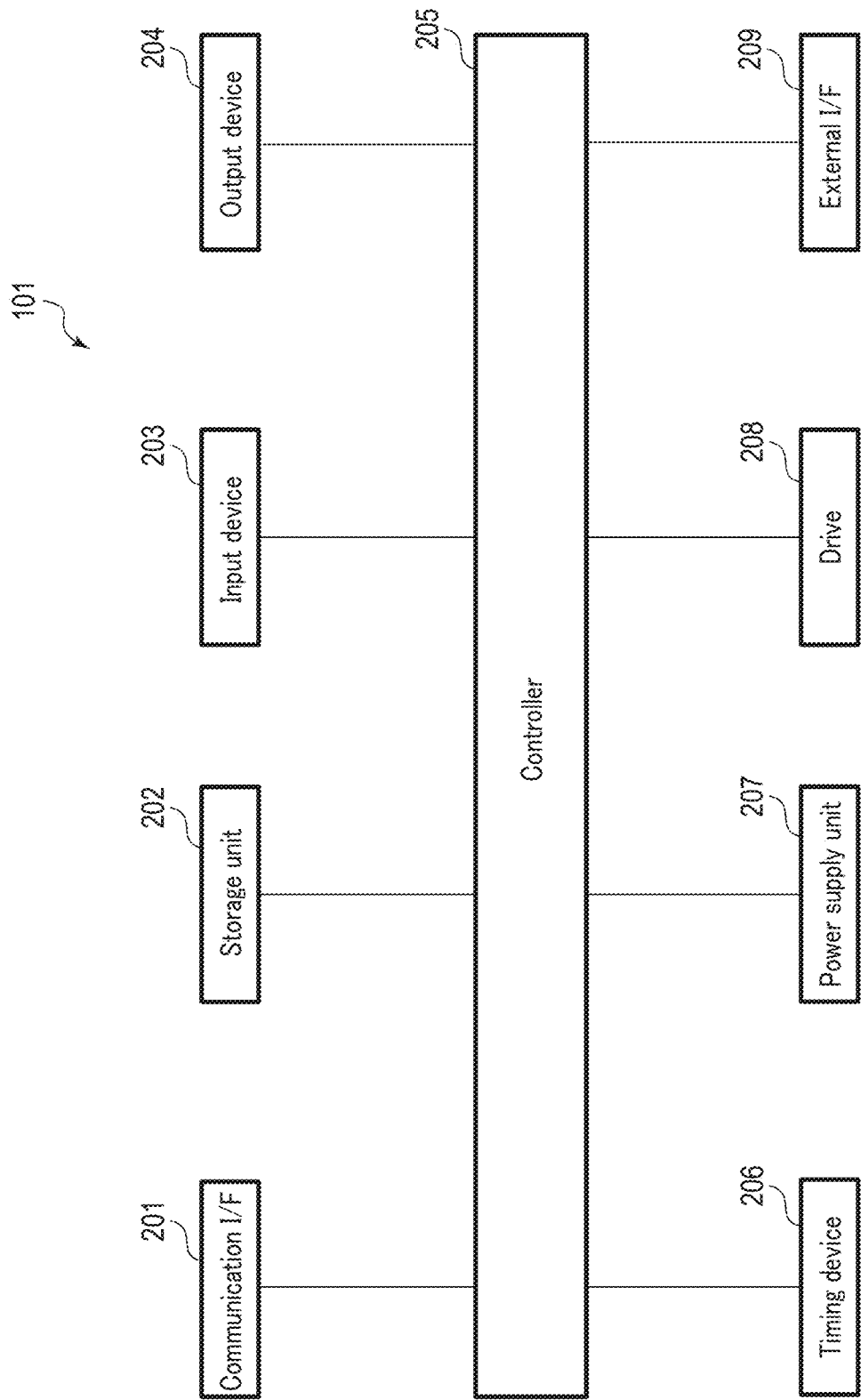
FIG. 2 is a diagram schematically showing an example of a hardware configuration of the document creation apparatus according to the embodiment.

As shown in FIG. 2, the document creation apparatus 101 according to the present embodiment includes a computer to which a communication interface 201, a storage unit 202, an input device 203, an output device 204, a controller 205, a timing device 206, a power supply unit 207, a drive 208, and an external interface 209 are electrically connected. The document creation apparatus 101 according to the present embodiment corresponds to the "document creation apparatus" of the present invention. In FIG. 2, the communication interface and the external interface are referred to as "Communication I/F" and "External I/F", respectively.

The communication interface 201 is, for example, a short-range wireless communication (e.g., Bluetooth (registered trademark)) module, a wired local area network (LAN) module, a wireless LAN module, etc., and is an interface for performing wired or wireless communication via a network. The communication interface 201 is an interface for connecting the document creation apparatus 101 to an external device (e.g., a computer, a server, or a communication device on a network). The communication interface 201 is controlled by the controller 205, receives medical data from the medical server 111 via the network 121, and/or receives insurance society data (e.g., health checkup data and/or health guidance data) from the insurance society server 112, and also transmits a document created by the document creation apparatus 101 to the smartphone 131 and/or the computer 132 via the network 121. The communication interface 201 may be for downloading a program to be executed by the document creation apparatus 101 from a specific server, etc. (not shown), or for uploading the program to the smartphone 131 and/or the computer 132, etc.

The communication via the network 121 may be either wireless or wired. Note that the network 121 may be an internetwork including the Internet, another type of network such as a hospital LAN, or one-to-one communication using a universal serial bus (USB) cable, etc. The communication interface 201 may include a micro USE connector.

The storage unit 202 is a medium that accumulates information such as programs through an electrical, magnetic, optical, mechanical, or chemical action in a manner that a computer or other devices, and machines, etc. can read the stored information such as programs. The storage unit 202, e.g., an auxiliary storage device such as a hard disk drive or a solid-state drive, stores medical examination propriety data and medical examination presence/absence data (medical data) acquired from the medical server 111; health checkup data, health guidance propriety data and health guidance presence/absence data (health guidance data), health consciousness data indicating a user health consciousness level, health knowledge data indicating a user knowledge level, and environment-related question and answer data acquired from the insurance society server 112; and an execution program for determining a type of user health based on these data and creating a document.

Further, the storage unit 202 stores document parts data (also referred to as "leaflet content data") used when the document creation unit 307 creates document data. The parts data includes, for example, classified document title data, portrait data (e.g., face shot data) of a person connected to a user of the document, document design data, feedback data such as diagram data corresponding to health checkup data and comment data for the health checkup data, expected behavior data for each type of user, and story data, each of which is, for example, associated with a health type.

The storage unit 202 may also store a program for adopting data with a high priority of being included in a document from the health checkup data. Furthermore, document data calculated by an execution program may be stored. The health checkup data is stored in the insurance society server 112 in this example, but may be stored in the medical server 111. Other data may also be stored in either the medical server 111 or the insurance society server 112 as appropriate.

The input device 203 is a device that accepts an input, and is, for example, a touch panel, a physical button, a mouse, a keyboard, etc. The output device 204 is a device that performs output, outputs information by display, sound, etc., and is, for example, a display, a speaker, etc.

The controller 205 includes a central processing unit (CPU), a random access memory (RAM), and/or a read only memory (ROM), and controls each element according to information processing. The controller 205 determines a health type of the user based. on the acquired health checkup data, health guidance data, health consciousness data, health knowledge data, and environment-related question and answer data, an execution program for creating a document suitable for the user is stored in the storage unit 202, and the controller 205 calls the execution program from the storage unit 202 and executes processing.

The timing device 206 is a device that measures time, and can measure date and time. For example, the timing device 206 is a clock including a calendar, and passes information on the current year/month and/or date/time to the controller 205.

The power supply unit 207 may be any unit as long as it can supply electric power, and is, for example, a rechargeable secondary battery or an AC power supply that can be obtained from a normal outlet. The power supply unit 207 supplies electric power to each element mounted on a main body of the document creation apparatus 101. The power supply unit 207 supplies electric power to, for example, the communication interface 201, storage unit 202, input device 203, output device 204, controller 205, timing device 206, drive 208, and external interface 209.

The drive 208 is a device for receiving stored data. (in particular for reading a program) from an auxiliary storage device, a recording medium, etc., and is, for example, a semiconductor memory drive (flash memory drive), a compact disk (CD) drive, a digital versatile disk (DVD) drive, etc. The type of the drive 208 may be appropriately selected according to the type of the storage medium. The above execution program and/or the data acquired from the medical server ill and the data acquired from the insurance society server 112, the parts data of the document, and/or the program for adopting high priority data, etc. may be stored in the storage medium.

The external interface 209 is for mediating between the main body of the document creation apparatus 101 and an external device, e.g., a USB port, and is an interface for connecting to the external device (e.g., a printer, a memory, or a communication device).

(Software Configuration)

<Document Creation Apparatus 101>

Figure 3:
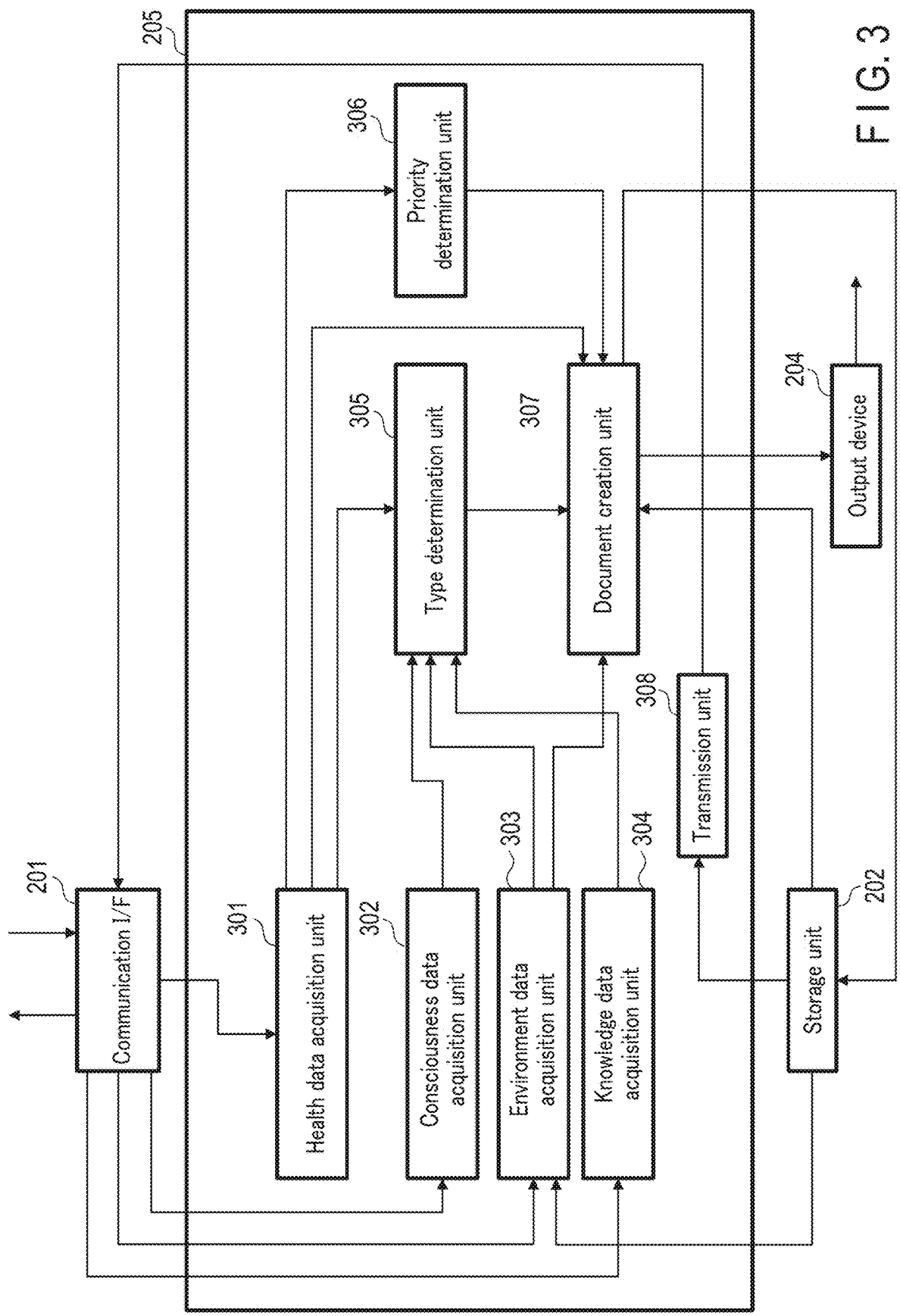
FIG. 3 is a diagram showing an example of a unit of a software configuration of the document creation apparatus according to the embodiment.

Next, an example of a software configuration of the document creation apparatus 101 according to the present embodiment will be described with reference to FIG. 3. FIG. 3 shows a software configuration for acquiring health checkup data of a user, health consciousness data of the user, environment-related question and answer data, and knowledge-related question and answer data, determining a type of the user health based on these data, and executing a program for creating a document to be presented to the user according to the type, executed by the controller 205 of the document creation apparatus 101.

When executing a necessary program, the controller 205 of the document creation apparatus 101 determines the type of the user health based on the data acquired from the medical server 111 and the insurance society server 112, which are stored in the storage unit 202, and develops an execution program for creating a document to be presented to the user according to the type in the RAM. Then, the controller 205 causes the CPU to interpret and execute the execution program for creating a document to be presented to the user according to the type, developed in the RAM, to control each element. As described above, as shown in FIG. 3, the document creation apparatus 101 according to the present embodiment includes a health data acquisition unit 301, a consciousness data acquisition unit 302, an environment data acquisition unit 303, a knowledge data acquisition unit 304, a type determination unit. 305, a priority determination unit 306, a document creation unit 307, and a transmission unit 308.

The health data acquisition unit 301 acquires health checkup data of a specific user from the external insurance society server 112 via the communication interface 201, and passes the health checkup data of the user to the type determination unit 305, priority determination unit 306, and document creation unit 307. In addition, the health data acquisition unit 301 may acquire the health checkup data of the user from any place other than the insurance society server 112 as long as the health checkup data of the user can be acquired.

The health checkup data is data which is digitized into one value for each user based on a value digitized for each item. A numerical value indicating the degree of health is set for each item, and this one value is determined based on these numerical values for respective items. As an example, a sum of the numerical values indicating the degree of health for respective items is set as this one value. As another example, one value is calculated by assigning a numerical value to each item according to whether the item is appropriate, attention required, or severe, and weighting the value with a priority assigned to each item. This priority is assigned to each item, with, for example, an item important for health being assigned a larger value. More specifically, to each item of health checkup data, for example, a positive value (e.g., +1) may be assigned when the data signifies "appropriate", a negative value (e.g., −1) may be assigned when the data signifies "attention required", and a smaller negative value (e.g., −2) may be assigned when the data signifies "severe". As for the priority, a positive value may be assigned so that the higher the priority, the larger the value, a product of a priority and a value to which the priority is assigned may be calculated for all the items, and a sum total of these products may be set as one value. In addition, the document creation unit 307 may create a document only for a certain item of health checkup data; in. this case, only that certain item (e.g., only blood pressure) of the health checkup data is used.

The consciousness data acquisition unit 302 acquires health consciousness data of the specific user from the external medical server 111 and/or insurance society server 112 via the communication interface 201, and passes the health consciousness data to the type determination unit 305. The health consciousness data is data on user health consciousness, and includes medical examination propriety data and medical examination presence/absence data (medical data) acquired from the medical server 111, and health guidance propriety data and health guidance presence/absence data (health guidance data) and question and answer data representing a question put to the user about health consciousness and the user's corresponding answer acquired from the insurance society server 112.

The medical data is data indicating whether or not a user undergoes a medical examination because an item indicating poor health is found among health checkup data, which leads to a doctor's medical examination; and, for example, a numerical value is assigned to the data depending on a medical examination propriety and if the user corresponds to the medical examination, whether the user undergoes the medical examination or not. As an example, a positive value (e.g., +1) is assigned to a case of not corresponding to a medical examination, a negative value (e.g., −1) is assigned to a case of corresponding to and undergoing the medical examination, and a smaller negative value (e.g., −2) is assigned to a case of corresponding to but not undergoing the medical examination.

The health guidance data is data indicating whether or not a user receives guidance from a public health nurse because an unhealthy item is found among health checkup data, which leads to the guidance; and, for example, a numerical value is assigned to the data depending on a health guidance propriety, and if the user corresponds to the health guidance, whether the user receives the health guidance or not. As an example, a positive value (e.g., +2) is assigned in a case of not corresponding to health guidance, a negative value (e.g., −3) is assigned in a case of corresponding to and receiving the health guidance, and a smaller negative value (e.g., −4) is assigned in a case of corresponding to but not receiving the health guidance.

The health consciousness-related question and answer data is data representing a question put to a user about health consciousness and a corresponding answer, where, for example, the user may be allowed to select, as an answer, one of two, three or more options for questions such as what the user thinks about their current health condition, whether the user pays attention to their health, whether the user has lost weight, whether the user regularly measures their weight, whether the user has undergone a health checkup during the last year, and whether the user has undergone a dental checkup during the last year, and a numerical value may be assigned to each option so as to digitize the health consciousness-related question and answer data.

The consciousness data acquisition unit 302 may determine a range by digitizing health consciousness data using one or more of the medical data, health guidance data, and health consciousness-related question and answer data to provide a threshold value, or may determine the range by classifying according to conditions. In the case of digitizing the health consciousness data, it is desirable to digitize the health consciousness data so that each possible item and one digitized numeral correspond one to one. For example, in the case where numerical values are assigned as in the above example, −1+(−4)=−5 corresponds to "a case of receiving a medical examination and not receiving health guidance", and +1+2=+3 corresponds to "a case of corresponding to neither a medical examination nor health guidance". On the contrary, a case of −5 corresponds only to the case of "receiving a medical examination and not receiving health guidance", and the case of +3 corresponds only to the case of "corresponding to neither a medical examination nor health guidance". If numerical values are assigned as health consciousness data in this way, it becomes possible to digitize all cases of medical data, health guidance data, and health consciousness-related question and answer data with scalar values, and these elements can be expressed by only one axis (one dimension). This idea can be similarly applied to environment-related question and answer data and health knowledge data to be described below.

The environment data acquisition unit 303 acquires environment-related question and answer data of a specific user from the external insurance society server 112 via the communication interface 201, passes the question and answer data to the type determination unit 305, further acquires data related to a user environment, other than that pertaining to the environment-related question and answer data, such as a whole body or face shot of a family member and/or a connected person in a company (e.g., a supervisor) from the storage unit 202, and passes the data to the document creation unit 307.

The environment-related question and answer data is data representing a question about a user health environment and a corresponding answer, where, for example, the user may be asked to choose an answer from two, three or more options for a question concerning a topic such as: whether to eat at a fairly fixed meal time per day; eat breakfast almost every day; eat nothing for two hours before bedtime; chew well and eat slowly; think about a dietary balance; have time to exercise during the week; consciously use stairs; walk faster than people of the same age and same sex; follow the guidance of a doctor about lifestyle; have parents or siblings with a lifestyle disease; have smoked someone else's cigarette in the past month or currently smoke; how often the user drinks and how often the user drinks more than 3 cups of sake per day; whether enough sleep or rest is obtained; and how many hours the user works a week, and whether or not this is shift work, and a numerical value may be assigned to each option so as to digitize the question and answer data about the user's health environment.

The knowledge data acquisition unit 304 acquires question and answer data about health knowledge of a specific user from the external insurance society server 112 via the communication interface 201, and passes the question and answer data to the type determination unit 305.

The knowledge-related question and answer data is data representing a question about user health knowledge and a corresponding answer, where, for example, the user may be asked to choose an answer from two, three or more options for a question concerning a topic such as: whether they know the disease(s) caused by smoking, know any beneficial substances in cigarette smoke; know of foods that are high in sodium; know the effects of taking potassium; know which foods contain potassium; know why beverages with added sucrose are not good for health; know which one of meat and fish is better for health and the reasons therefor; know of a relationship between drinking and increased blood pressure; and know of a relationship between cooking oil and increased blood pressure, and a numerical value may be assigned to each option so as to digitize the question and answer data about the user's health knowledge.

The type determination unit 305 acquires, for a specific user, health checkup data from the health data acquisition unit 301, health consciousness data from the consciousness data acquisition unit 302, environment-related question and answer data from the environment data acquisition unit 303, and knowledge-related question and answer data from the knowledge data acquisition unit 304, and determines a type related to health of the user.

According to data content of each of the health checkup data, health consciousness data, environment-related question and answer data, and knowledge-related question and answer data, the type determination unit 305 classifies cases into a plurality of ranges. Then, the type determination unit 305 combines these four types of data classified into the ranges to further classify the ranges into cases, and determines one type for each classified range. Specifically, for example, the data is classified into three ranges of "normal", "attention required", and "severe" based on the health checkup data; into two ranges of high consciousness and low consciousness based on the health consciousness data; into two ranges of healthy environment and unhealthy environment based on the environment-related question and answer data; and into three ranges of high knowledge level, normal knowledge level, and low knowledge level based on the knowledge-related question and answer data in advance, and the type determination unit 305 can then determine the type among the 3×2×2×3=36 types to which the user belongs, based on the four pieces of user data. Here, the type determination unit 305 uses all of the four pieces of data, but the type determination may be performed using the health checkup data and any one or more pieces of data among the other three pieces of data. For example, in a case where the determination is performed using the health checkup data and the environment-related question and answer data, the type determination unit 305 determines the type among 3×2=6 types to which the user belongs.

In addition, as a method for determining the range to correspond to, a condition may be set for each range, and the range to which the user belongs may be determined according to whether the user corresponds to the condition. In addition, as described in the above data acquisition, a range may be set by digitizing each data and setting one or more threshold values for each data.

The type determination unit 305 determines, in a four-dimensional space spanned by a vector corresponding to a value obtained by digitizing health checkup data and three vectors corresponding to values obtained by digitizing health consciousness data, environment-related question and answer data, and knowledge-related question and answer data, a user health type according to where these user data are located.

Alternatively, for example, the data may be multi-dimensionalized into a vector corresponding to a value for each item of health checkup data, and three vectors corresponding to respective values of the medical data of health consciousness data, health guidance data, and question and answer data representing a question put to a user about health consciousness and the user's corresponding answer. In this case where the health checkup data and the health consciousness data are acquired, if the number of health checkup data items is n and the number of health consciousness data types is 3, a space determined by the type determination unit 305 is an (n+3)-dimensional space spanned by (n+3) vectors, and the type determination unit 305 determines the user type using this space. As described above, the space used by the type determination unit 305 for the type determination is not limited to four dimensions or less, and the type determination may be performed in a multi-dimensional space of five dimensions or more.

As the priority of the data included in the health checkup data acquired from the health data acquisition unit 301 is higher, the priority determination unit 306 attempts to include content related to this data in a document to be created by the document creation unit 307, and determines which data is to be adopted by comparing the content with the limit of an amount of content that can be included in the document and/or a threshold value of the priority to be set. Before the document creation unit 307 refers to leaflet content data stored in the storage unit 202 to decide document data, the priority determination unit 306 determines data included in the health checkup data to be adopted by the priority determination unit 306 as the document data. A plurality of types of document templates may be stored in the storage unit 202, and in this case, a template corresponding to data decided for adoption by the priority determination unit 306 is, for example, adopted by the document creation unit 307. The template may indicate detailed data such as a graph, only a small amount of approximate numerical values, or only simple words without indicating any numerical values. The selection of the template may be determined according to a knowledge level related to the user health that can be determined by health knowledge data (knowledge-related question and answer data).

As a method for determining whether or not the priority determination unit 306 adopts data, for example, in a case where the amount of data is too large to be included in a document with an initially set threshold value, the threshold value may be increased by a predetermined amount, and data to be adopted in the document may be re-determined based on the set priority. On the contrary, if the amount of data is too small for an initially set threshold value and there is a space in a document, the threshold value may be lowered by a predetermined amount, and data to be adopted in the document may be re-determined based on the set priority.

The priority is assigned to each data included in the health checkup data in advance. However, the priority determination unit 306 may assign a priority to each data included in the health checkup data. In the case where the priority is assigned, items (e.g., blood pressure value, blood test items (liver function test, blood lipid test, blood glucose test), urine test, and anemia test) are assigned to the data included in the health checkup data.

Therefore, the priority determination unit 306 can determine the priority for each item. Further, the priority may be determined for each user. For example, the priority of the liver function test is set to be highest for a user for whom the liver function test is important. In addition, the priority determination unit 306 may determine the priority by appropriately changing a determination criterion such as setting the priority of an item essential to the specific health checkup, the occupational safety and hygiene law, the school health safety law, etc. to be higher than that of other items, and applying it to the health checkup data.

Based on the type determined by the type determination unit 305, the document creation unit 307 creates document data for a document for presentation to the user by using the health checkup data acquired from the health data acquisition unit 301, the environment-related question and answer data acquired from the environment data acquisition unit 303, data about environment other than the question and answer data stored in the storage unit 202, and the parts data of the document used when creating the document data. Note that the document creation unit 307 may create the document data using only the health checkup data or only the environment-related question and answer data based on the type.

The transmission unit 303 transmits document data stored in the storage unit 202 to a terminal of a user, etc. via the communication interface 201.

<Others>

The operation of the document creation apparatus 101 will be described in detail in an operation example to be described later. In the present embodiment, the controller 205 of the document creation apparatus 101 may be implemented by a general-purpose CPU. However, some or all of the above operations (or functions) may be implemented by one or more dedicated processors. The configuration of the document creation apparatus 101 may be omitted, replaced, or added as appropriate according to the embodiment.

[Operation Example: Overall]

Next, with reference to FIG. 4, a description will be given of an example of a processing procedure for acquiring data, determining a type of a user based on these data, creating document data to be presented to the user based on the type, and transmitting the document data to a user terminal in a case where the document creation apparatus 101 is used.

FIG. 4 is a flowchart illustrating an example of a processing procedure of the document creation apparatus 101. The processing procedure described below is merely an example, and each process may be changed where deemed possible to do so in the processing procedure described below, steps can be omitted, replaced, and added as appropriate according to the embodiment.

(Activation)

First, a user or an administrator activates the document creation apparatus 101 via the input device 203, and further accepts an input such as a setting. The controller 205 of the document creation apparatus 101 proceeds with processing according to the following processing procedure.

(Step S401)

In step S401, the controller 205 operates as the health data acquisition unit 301 and the consciousness data acquisition unit 302. The health data acquisition unit 301 acquires health checkup data and health guidance propriety data indicating whether or not a user corresponds to the receiving of health guidance among health guidance data from the insurance society server 112 via the communication interface 201. The consciousness data acquisition unit 302 acquires medical examination propriety data indicating whether or not the user corresponds to a medical examination among medical data from the medical server 111 via the communication interface 201.

(Step S402)

In step S402, the controller 205 operates as the consciousness data acquisition unit 302, and acquires, from the medical server 111 and the insurance society server 112 via the communication interface 201, medical examination presence/absence data indicating whether the user receives a medical examination among the medical data and health guidance data indicating whether the user receives health guidance.

(Step S403)

In step S403, the controller 205 operates as the consciousness data acquisition unit 302. The consciousness data acquisition unit 302 acquires question and answer data representing a question put to the user about user health consciousness and the user's corresponding answer from the insurance society server 112 via the communication interface 201.

(Step S404)

In step S404, the controller 205 operates as the environment data acquisition unit 303. The environment data acquisition unit 303 acquires question and answer data representing a question about a health environment of the user and an answer to the question from the insurance society server 112 via the communication interface 201.

(Step S405)

In step S405, the controller 205 operates as the knowledge data acquisition unit 304, and acquires question and answer data representing a question about health knowledge of the user and an answer to the question from the insurance society server 112 via the communication interface 201.

(Step S406)

In step S406, the controller 205 operates as the type determination unit 305, and determines a health type of the user based on the data acquired in steps S401, S402, S403, S404, and S405.

(Step S407)

In step S407, the controller 205 operates as the document creation unit 307, and acquires, from the storage unit 202, data other than the environment-related question and answer data related to an environment of the user (e.g., face shots of a family member and a supervisor of the user) and design data of a document. Then, the document creation unit 307 uses these acquired data, the health checkup data acquired in step S401, and the question and answer data representing a question about the health environment of the user and an answer to the question acquired in step S404 to create leaflet data (document data) based on the health type of the user determined in step S406. The created leaflet data is stored in the storage unit 202 by the document creation unit 307 as individual leaflet data.

(Step S408)

In step S408, the controller 205 operates as the transmission unit 308, and transmits the leaflet data from the storage unit 202 to the user terminal via the communication interface 201.

[Operation Example; Health Type Determination]

Next, with reference to FIG. 5, a description will be given of an example of a processing procedure in a case where the type determination unit 305 determines the health type of the user based on, as an example, the medical data. and the health guidance data acquired from the health data acquisition unit 301.

Figure 5:
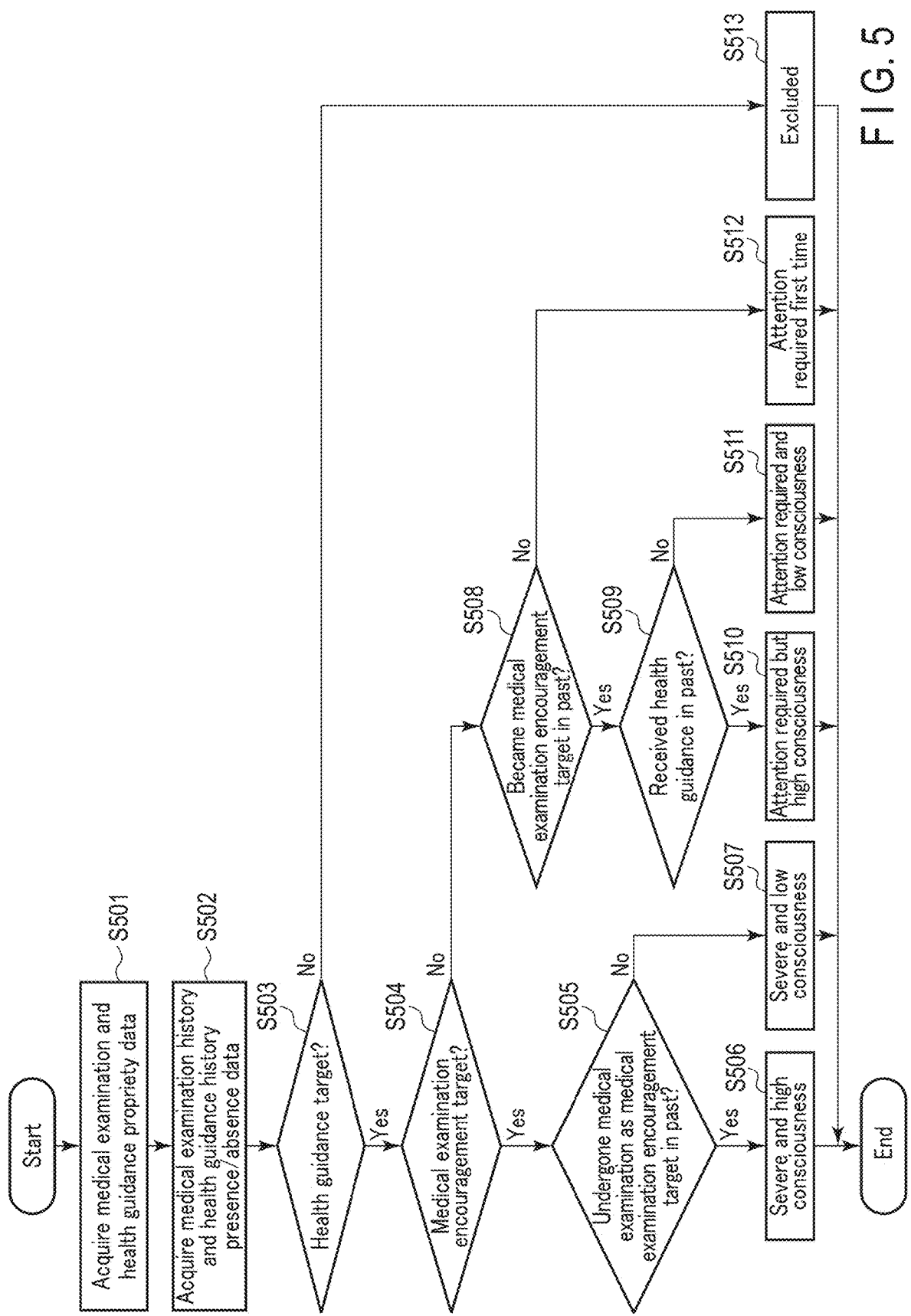
FIG. 5 is a flowchart schematically showing an example of a processing procedure of step S406 in FIG. 4.

FIG. 5 is a flowchart illustrating an example of a processing procedure of the health data acquisition unit 301 and the type determination unit 305. The processing procedure described below is merely an example, and each process may be changed where deemed possible to do so. In the processing procedure described below, steps can be omitted, replaced, and added as appropriate according to the embodiment.

(Step S501)

In step S501, the controller 205 operates as the health data acquisition unit 301, and acquires, from the medical server 111 and the insurance society server 112 via the communication interface 201, medical examination propriety data indicating whether or not a user corresponds to a target to be examined and health guidance propriety data indicating whether or not the user corresponds to a target who should receive health guidance.

(Step S502)

In step S502, the controller 205 operates as the health data acquisition unit 301, and acquires, from the medical server 111 via the communication interface 201, medical examination history presence/absence data indicating, if the user corresponds to the target to be examined, whether or not the user has undergone a medical examination in the past and acquires, from the insurance society server 112, health guidance history presence/absence data indicating, if the user corresponds to the target who should receive health guidance, whether or not the user has received health guidance in the past.

(Step S503)

In step S503, the controller 205 operates as the type determination unit 305, refers to the health guidance propriety data, determines whether or not the concerned user is the health guidance target, proceeds to step S504 if applicable, and proceeds to step S513 if not applicable.

(Step S504)

In step S504, the controller 205 operates as the type determination unit 305, refers to the medical examination propriety data, determines whether or not the user is a target who is encouraged to undergo a medical examination, proceeds to step S505 if applicable, and proceeds to step S508 if not applicable.

(Step S505)

In step S505, the controller 205 operates as the type determination unit 305, refers to the medical examination history presence/absence data, determines whether or not the user undergoes a medical examination as a medical examination target in the past, proceeds to step S506 if applicable, and proceeds to step S507 if not applicable. Instead of referring to the medical examination history presence/absence data, the controller 205 may determine whether or not the user has received health guidance in the past and proceed to step S506 if the user has received prior health guidance, and proceed to step S507 if this is not the case.

(Step S506)

In step S506, the controller 205 operates as the type determination unit 305, determines that a user health condition is considerably had but that user health consciousness is high, and passes a determination result of "severe and high consciousness" to the document creation unit 307.

(Step S507)

In step S507, the controller 205 operates as the type determination unit 305, determines that the user health condition is considerably bad and that the user health consciousness is low, and passes a determination result of "severe and low consciousness" to the document creation unit 307.

(Step S508)

In step S508, the controller 205 operates as the type determination unit 305, refers to the medical examination history presence/absence data, determines whether or not the user has become a target for undergoing a medical examination in the past, proceeds to step S509 if this is the case, and proceeds to step S512 if this is not the case.

(Step S509)

In step S509, the controller 205 operates as the type determination unit 305, refers to past health guidance history presence/absence data, determines whether or not the user has received health guidance in the past, proceeds to step S510 if this is the case, and proceeds to step S511 if this is not the case.

(Step S510)

In step S510, the controller 205 operates as the type determination unit 305, determines that the health condition of the user may deteriorate but that the user health consciousness is high, and passes a determination result of "attention required and high consciousness" to the document creation unit 307.

(Step S511)

In step S511, the controller 205 operates as the type determination unit 305, determines that the user health condition may deteriorate and that the user health consciousness is low, and passes a determination result. of "attention required and low consciousness" to the document creation unit 307.

(Step S512)

In step S512, the controller 205 operates as the type determination unit 305, determines that the user health condition may deteriorate but that the user health consciousness is undetermined, and passes a determination result of "attention required and first time" to the document creation unit 307.

(Step S513)

In step S513, the controller 205 operates as the type determination unit 305 and determines that the user health condition is good, and is therefore excluded here.

[Operation Example: Data Selection Based on Priority]

Next, an example of a processing procedure in which the priority determination unit 306 selects data for inclusion in the document data from data included in the health checkup data, based on priority, will be described with reference to FIG. 6. Here, as described with reference to FIG. 3, it is assumed that priority is assigned to each data for each item included in the health checkup data.

Figure 6:
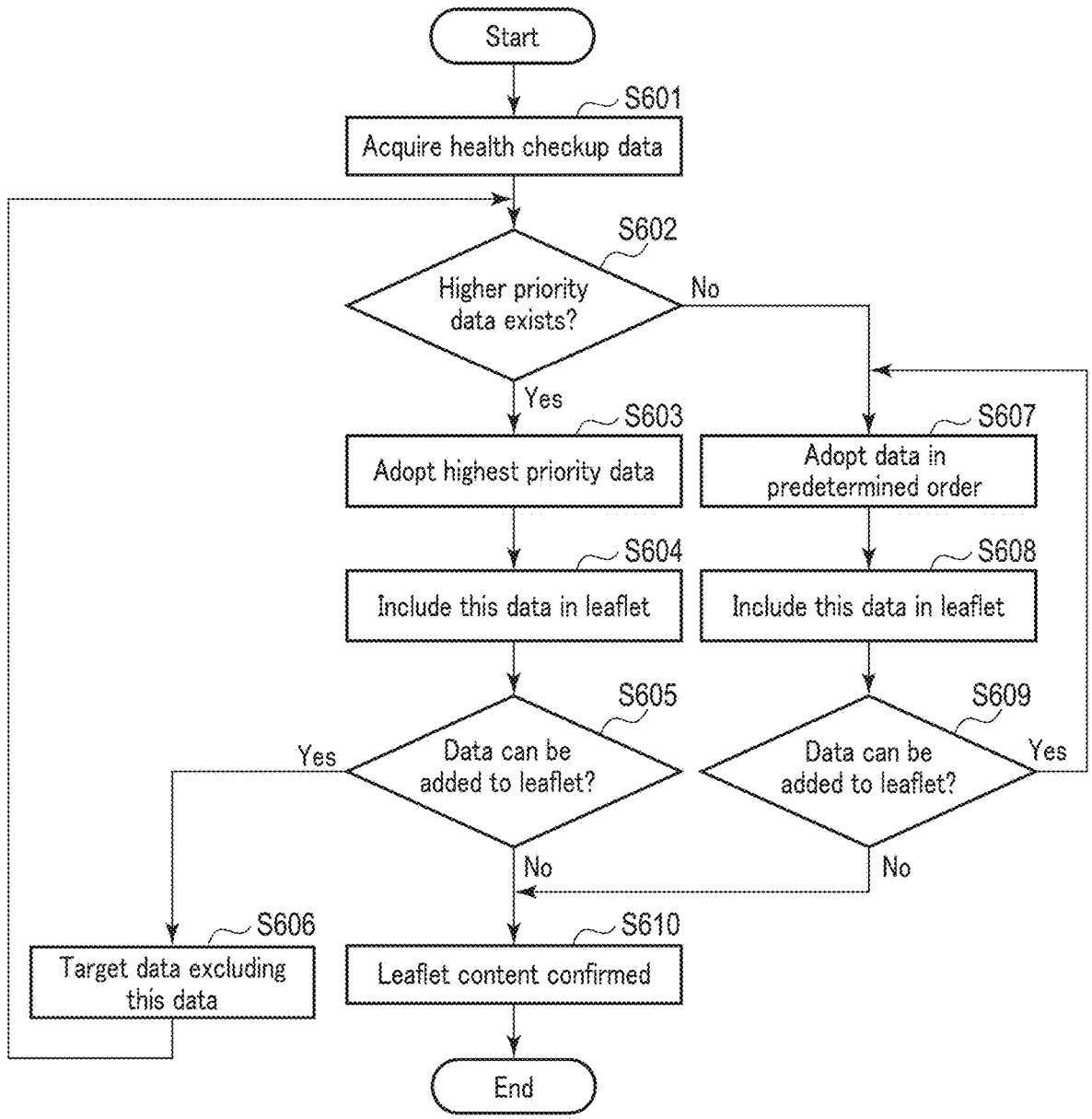
FIG. 6 is a flowchart schematically showing an example of a processing procedure related to a priority determination unit of FIG. 3.

FIG. 6 is a flowchart showing an example of a processing procedure of the health data acquisition unit 301 and the priority determination unit 306. The processing procedure described below is merely an example, and each process may be changed where deemed possible to do so. In the processing procedure described below, steps can be omitted, replaced, and added as appropriate according to the embodiment.

(Step S601)

In step S601, the controller 205 operates as the health data acquisition unit 301 and the priority determination unit 306, determines whether or not the health checkup data includes data having a priority higher than a threshold value, proceeds to step S603 if there is higher priority data, and proceeds to step S607 if there is no higher priority data.

(Step S602)

In step S602, the controller 205 operates as the priority determination unit 306, determines, on data included in the health checkup data, whether or not there exists data having a higher priority than the priority as a threshold value, proceeds to step S603 if there is higher priority data, and proceeds to step S607 if there is no higher priority data.

(Step S603)

In step S603, the controller 205 operates as the priority determination unit 306, and determines to adopt, among the data determined to be data having a higher priority in step S602, data having the highest priority as document data.

(Step S604)

In step S604, the controller 205 operates as the priority determination unit 306, and passes to the document creation unit 307 the data determined to be adopted in step S603 as to be included in a leaflet.

(Step S605)

In step S605, the controller 205 operates as the priority determination unit 306, determines whether or not the data to be included in the leaflet in step S604 can be added to the leaflet, proceeds to step S606 if it is determined that it can, and proceeds to step S610 if it is determined that it cannot. This determination may be performed by the document creation unit 307, and the determination result may be returned to the priority determination unit 306.

(Step S606)

In step S606, the controller 205 operates as the priority determination unit 306, and returns to step S602 by excluding the data determined to be addable to the leaflet in step S605 from target data and by regarding the remaining data as target data.

(Step S607)

In step S607, the controller 205 operates as the priority determination unit 306, and determines adoption of data in a predetermined order set in advance since there is no data having a higher priority. For example, data may be adopted from the health checkup data based on the user health environment data. Specifically, for example, a health checkup data item to which the user should particularly pay attention may be selected from the user health environment data or set in advance so as to adopt corresponding data. In addition, an item related to a disease peculiar to the user's area of residence may be adopted.

(Step S608)

In step S608, the controller 205 operates as the priority determination unit 306, and passes to the document creation unit 307 the data determined to be adopted in step S607 as to be included in a leaflet.

(Step S609)

In step S609, the controller 205 operates as the priority determination unit 306, determines whether or not the data to be included in the leaflet in step S608 can be added to the leaflet, proceeds to step S607 if it is determined that it can, and proceeds to step S610 if it is determined that it cannot. The document creation unit 307 may determine whether or not the data can be added, and return the determination result to the priority determination unit 306.

(Step S610)

In step S610, the controller 205 operates as the priority determination, unit 306, and determines that content (data) to be included in the leaflet is confirmed at this moment since no more data can be added. This determination may be performed by the document creation unit 307, and the determination result may be returned to the priority determination unit 306.

Note that the processing by the steps in FIG. 6. described above is performed, for example, before the document creation unit 307 refers to the leaflet data stored in the storage unit 202, and the data is to be used for the leaflet is determined in advance. Content of a template may be determined in association either with the content of the data determined here or with the content of the user knowledge data.

[Example using Two Axes; Two-Dimensional Space]

Hereinafter, with reference to FIGS. 7A, 7B, 7C, 8, and 9, a description will be given of a case where the type determination unit 305 determines the health type of the user based on the health checkup data acquired by the health data acquisition unit 301 and the health consciousness data acquired by the consciousness data acquisition unit 302, and the document creation unit 307 creates leaflet data that is the document data to be presented to the user. In this example, blood pressure value data is used as the health checkup data, and medical data and health guidance data are used as the health consciousness data.

Figure 7A:
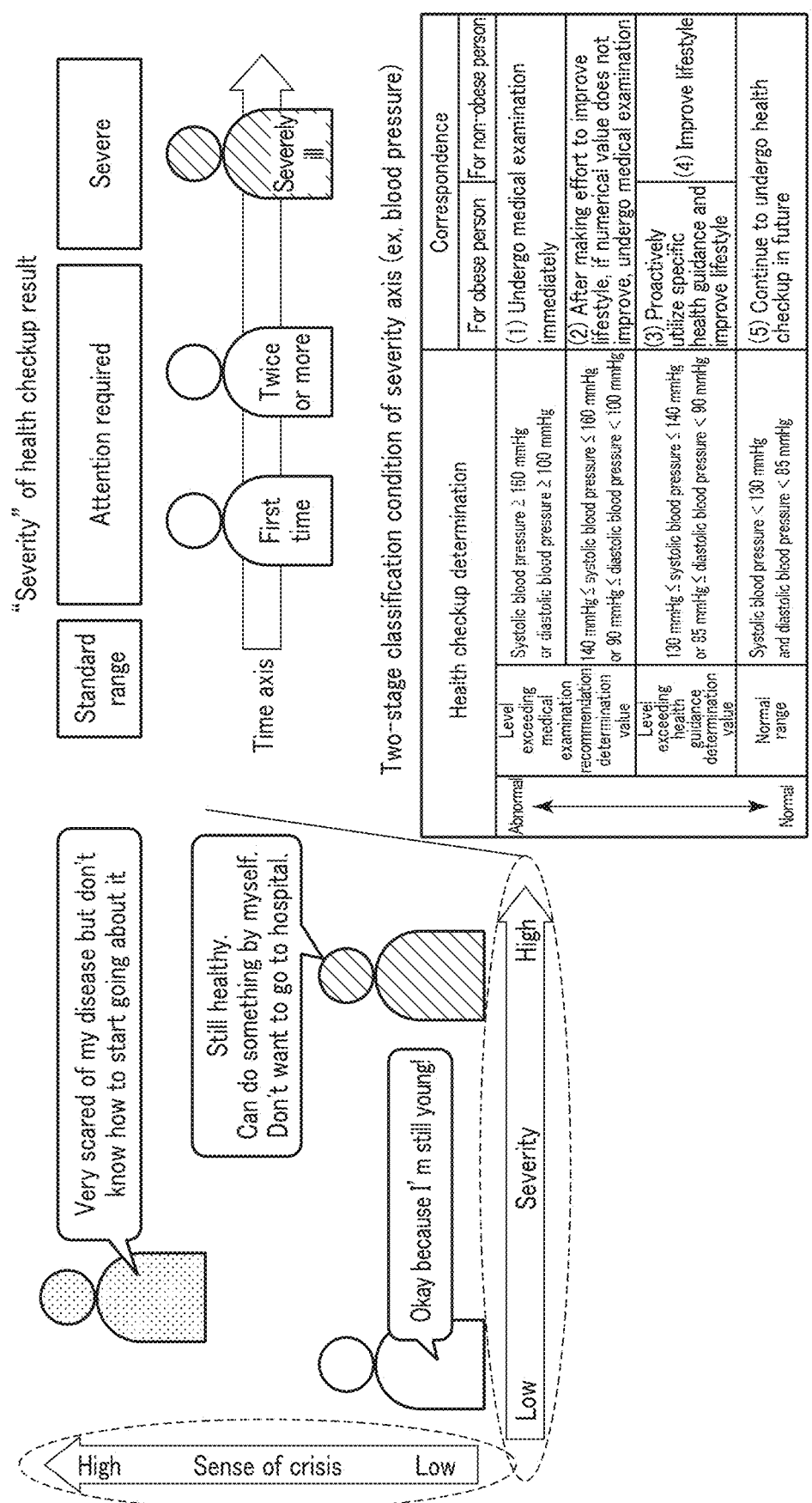
FIG. 7A is a diagram showing an example of severity in a case where a type related to user health is determined based on two axes of severity and sense of crisis.

A first axis (a horizontal axis in this example) indicates severity based on the health checkup data as shown in FIG. 7A. The severity is determined based on the blood pressure value data in this example, and classified into "normal range", "level exceeding health guidance determination value", and "level exceeding medical examination recommendation determination value". In this example, "level exceeding health guidance determination value" corresponds to attention required, and "level exceeding medical examination recommendation determination value" corresponds to severe. Furthermore, when determined to be "attention required", it is classified according to whether the number of times this determination result is received is one, two or more. For the sake of simplicity in this example, the severity is determined only by the blood pressure value, but it may be determined by referring to whether the user is obese, a value of lipid and/or carbohydrate in a blood test result item of the user, etc.

Figure 7B:
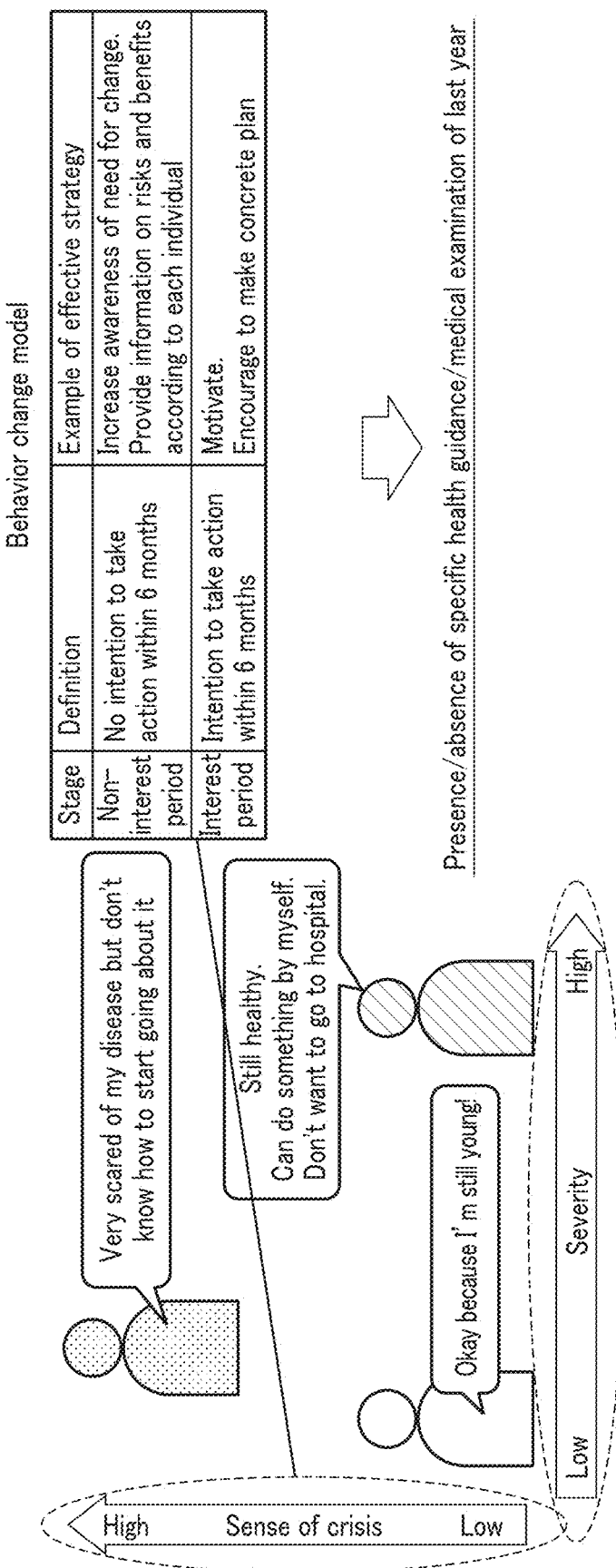
FIG. 7B is a diagram showing an example of the sense of crisis in the case where the type related to the user health is determined based on the two axes of severity and sense of crisis.

As shown in FIG. 7B, a second axis (a vertical axis in this example) indicates sense of crisis based on the health consciousness data. The sense of crisis can be determined based on, for example, the fact that it is low in a non-interest period of a behavior change model and high in an interest period in this example, it is determined based on the medical data and the health guidance data, and classified by determining whether or not a sense of crisis exists depending on whether or not the user has received health guidance during the last year, or whether or not the user has undergone a medical examination in a medical institution. In a case of receiving health guidance or undergoing a medical examination in a medical institution, it is determined that the sense of crisis is high, and in a case of not receiving the health guidance or undergoing the medical examination in the medical institution even though recommended, it is determined that the sense of crisis is low. The degree of sense of crisis is not limited to two, and may be classified more finely. For example, it may be determined that the user's sense of crisis is lower in a case of not undergoing a medical examination in a medical institution despite recommendation as compared to a case of not receiving health guidance despite recommendation. Other than that, as described above, the sense of crisis may be determined in detail based on the health consciousness-related question and answer data, which is the health consciousness data. Based on this question and answer data, whether it is a non-interest or interest period may be determined, with the sense of crisis being low in the non-interest period and high in the interest period.

As shown in FIG. 7C, the type determination unit. 305 performs type classification according to the values of the first and second axes in the first axis, it is determined to be "attention required" in a case where the blood pressure value data falls within a range recommended for health guidance and "severe" in a case where the blood pressure value data falls within a range recommended for a medical examination in a medical institution, and the "attention required" is further classified into a case where applicable for the first time and a case where applicable more than once. In the second axis, it is classified according to whether past health guidance or medical examination in a medical institution was conducted or not (according to health guidance data or medical data of the last year in this example). With these two axes, the type determination unit 305 can classify into five health types as shown in FIG. 7C. In this example, there are types (1) to (5), and each type has its own characteristic which is described in FIG. 7D. For example, among them, the type (4) is lowest in the priority order of health, i.e., a type most requiring health improvement.

Next, the document creation unit 307 creates document data for a document for presentation to the user according to the classified types. As an example, FIG. 8 shows an outline of a title and content included in the document data for each type, and examples of facial expressions. FIG. 9 shows an example of a leaflet created based on the content of the table in FIG. 8.

As shown in FIG. 8, the title of the document and the content of the document are determined for each health type. The content is to be transmitted to the user, and include, for example, feedback of a health checkup data result, presentation of an expected user behavior, and a future story. In the feedback of the health checkup data result, according to a health checkup result for each user, content indicating its severity is presented. The expected user behavior is presented to the user to either indicate what to do or continue an existing behavior if the user has already shown a good behavior. The story is presented in anticipation of the most likely event for the user in the future estimated from the current state, and, for example, either one of a story with good content (a Good story) and a story with bad content (a Bad story) is presented. Furthermore, the document data includes face shot data of a person connected to the user, with the facial expression changing according to the health type of the user.

For example, in the case of types (3) and (5), the health checkup data indicates "attention required" or "severe", but the type shows "conducted" indicating that a medical examination has been undergone or health guidance has been received. Thus, the user is already aware of the health checkup data not being good and has either undergone a medical examination or received health guidance. Therefore, it is not particularly necessary to express an emotion, and so the facial expression is a "expressionless". In the case of type (1), the health checkup data indicates "attention required", but the user has undergone the health checkup for the first time, and therefore inevitably has not undergone a medical examination or received health guidance. Accordingly, the facial expression is "sad" expressing only the fact that the health condition of the user is "attention required". In the case of type (2), the health checkup data indicates "attention required", but the type shows "not conducted" indicating that the user has not undergone a medical examination or received health guidance. Thus, the user is aware of the health checkup data not being good but has not undergone a medical examination and received health guidance. Since the user is aware of their health not being good but does not take any relevant measures, the facial expression is "dislike". In the case of type (4), since the health checkup data indicates "severe" and, furthermore, the type shows "not conducted" indicating that no medical examination has been undergone or health guidance received, the user is already aware of the health checkup data not being good, and they have severe symptoms, and they have not undergone a medical examination. or received health. guidance. Accordingly, since the user is seriously ill according to the health checkup data and has not undergone a medical examination and received health guidance, the facial expression is "anger", which is worse than dislike.

Next, with reference to FIG. 9, a description will be given of an example of a leaflet in a case where the document creation unit 307 creates leaflet data based on the table of FIG. 8.

The document creation unit 307 determines the title, content, and facial expression as shown in FIG. 8 according to the type determined by the type determination unit 305, and creates a leaflet for presentation to the user based on these data. As shown in the left of FIG. 9, a title is placed on a cover of the leaflet, and a person expressing the facial expression data described in FIG. 8 is placed beside the title to impress the user. Furthermore, as shown in the right of FIG. 9, details corresponding to the content are described. In the example shown in FIG. 9, feedback data of the health checkup data of the user is displayed together with a diagram as content 1, an expected user behavior is presented as content 2, and a story is presented based on the health type of the user as content 3.

As described above, the document creation unit 307 creates the leaflet data (document data) for presentation to the user according to the health type of the user and the health checkup data, so that the user can be effectively aware of their own health condition. This increases a possibility that the user is actively involved in a medical examination in a medical institution or health guidance, thereby improving or maintaining their health in a favorable condition.

[Document. Creation Unit 307]

Hereinafter, a description will be given of a detailed example of a processing procedure related to the document creation unit 307 with reference to FIGS. 10, 11, 12, 13, 14, 15, 16, 17, and 18. FIG. 10 is a table related to health checkup data and health consciousness data to be input by the document creation unit 307. In this example, the case in the above-described "two-dimensional space" is assumed in which the health type of the user is determined by the type determination unit 305 based on the health checkup data and the health consciousness data acquired by the health data acquisition unit 301 and the consciousness data acquisition unit 302. That is, the data to be input by the type determination unit 305 are the blood pressure value data, medical data, and health guidance data shown in FIGS. 7A and 7E, and the type determination results are the above-described five types (1) to (5).

With reference to FIG. 10, a description will be given of an example of the health checkup data, the medical data and health guidance data, and portrait data (e.g., face shot data) of a person connected to the user acquired by the environment data acquisition unit 303 from the storage unit 202.

As shown in FIG. 10, the health checkup data includes past data to current data, and data of respective items (e.g., blood pressure, weight, etc.) are described in each health checkup result. In the medical data and health guidance data, "Yes" or "No" describe whether or not a medical examination is undergone and/or whether or not health guidance is received as an actual result, and medical examination propriety data (applicable or nonapplicable) indicating whether or not the user is determined to further require a medical examination, and health guidance propriety data (applicable or nonapplicable) indicating whether or not the user is determined to require health guidance are described.

Furthermore, information and face shot data of a person connected to the user are registered in advance in the storage unit 202, and this data is registered together with priorities indicating a priority order for use of the face shot. The document creation unit 307 refers to the storage unit 202 to determine the face shot to be included in the document according to the health type as shown in FIG. 8, but may determine it with reference to this priority.

[Operation Example of Document Creation Unit 307: Details of S406]

Figure 11:
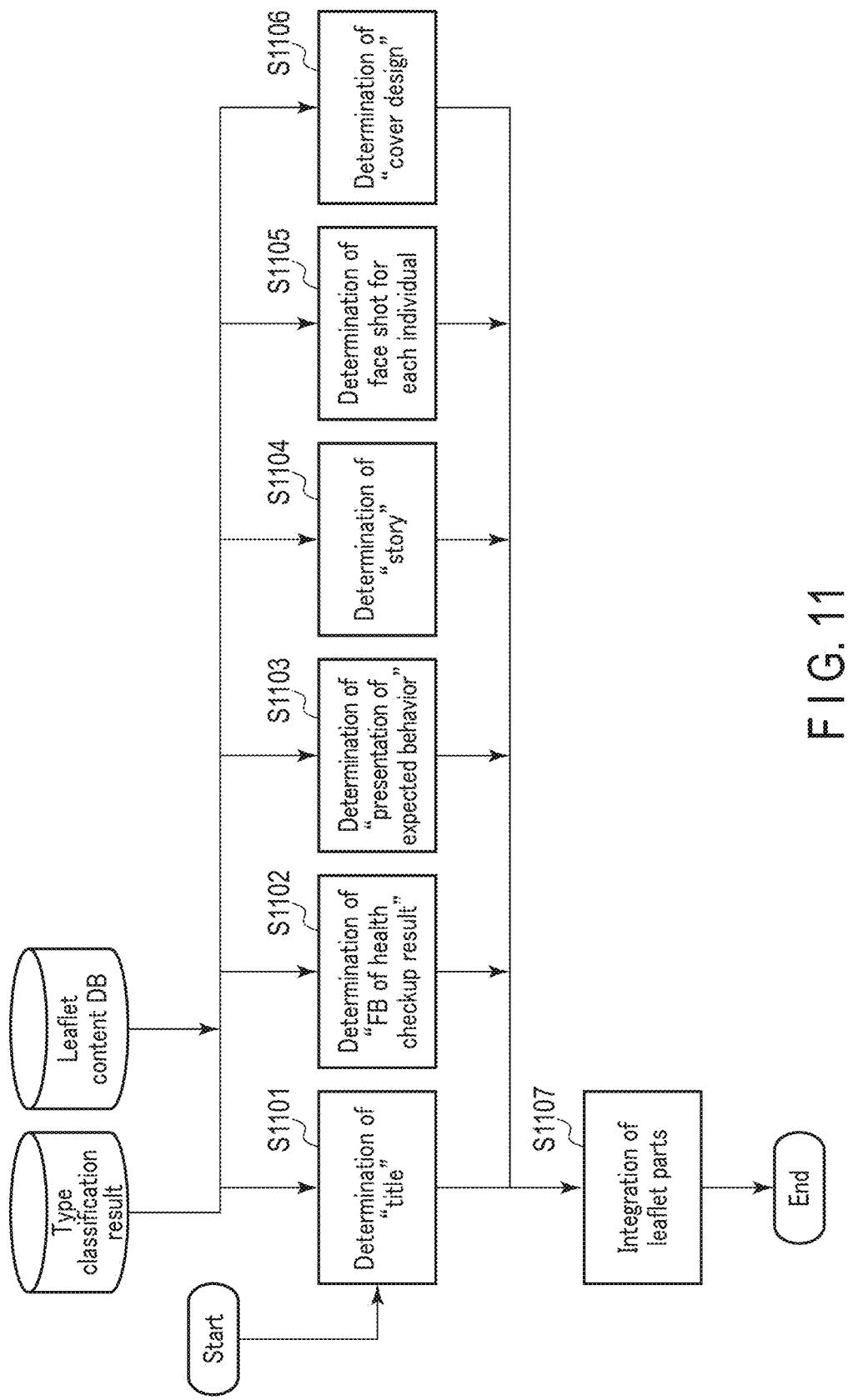
FIG. 11 is a flowchart schematically showing an example of a processing procedure related to the document creation unit of FIG. 3.

Next, with reference to FIG. 11, a description will be given of an example of a processing procedure of step S403 in FIG. 5 regarding the document creation unit 307. Each step will be described with reference to FIGS. 12, 13, 14, 15, 16, 17, and 18 as appropriate.

(Step S1101)

In step S1101, the controller 205 operates as the document creation unit 307, and a title is determined in accordance with the document title data registered as the data of the leaflet stored in the storage unit 202 and the type classification result determined by the type determination unit 305. FIG. 12 shows an example of a table in which this title of the document is associated with the type classification result.

The storage unit 202 stores a table in which a title and its explanation are associated with each other according to the determined health type. This table has, for example, the content shown in FIG. 12, and includes classification (corresponding to the health type), content (corresponding to the title), and descriptions of the content. These data of the table are set so that they may be changed or added to, and can be changed by an administrator, etc.

(Step S1102)

In step S1102, the controller 205 operates as the document creation unit 307, and determines, in accordance with the health checkup data acquired by the health data acquisition unit 301, data to be used as feedback data of a health checkup result registered as the leaflet content data stored in the storage unit 202. For example, the kind of diagram used and the kind of comment added are determined as the feedback data. The feedback data such as a diagram to be used may be changed corresponding to the type classification result determined by the type determination unit 305.

Figure 13:
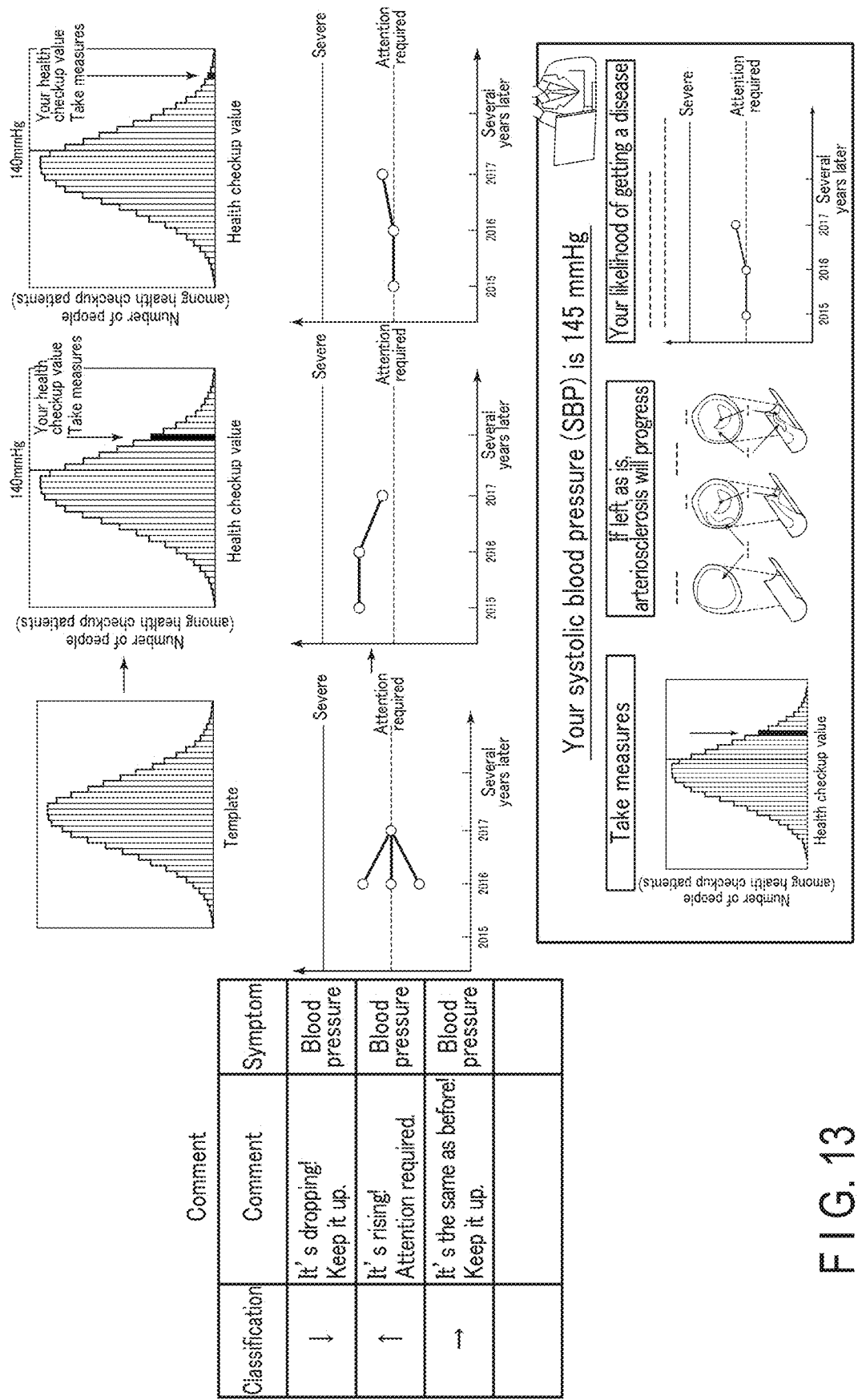
FIG. 13 is a diagram showing sample feedback data (FB) of a health checkup result in step S1102 of FIG. 11.

Examples of the feedback data used by the document creation unit 307 based on the health checkup data include comments, a template of a distribution map, a template of an aging graph, and advice data based on blood pressure value shown in FIG. 13.

The storage unit 202 stores a template of a distribution map, a template showing a temporal change, and a template for adding a comment according to health checkup data as shown in. FIG. 13, determines a corresponding template according to the health type and the health checkup data, and incorporates the content to be set as unit of document data.

(Step S1103)

In step S1103, the controller 205 operates as the document creation unit 307, and expected user behavior content is determined for each type by a table in which presentation data of expected behavior is associated with the type classification result determined by the type determination unit 305, registered as the leaflet content data stored in the storage unit 202.

The storage unit 202 stores the leaflet content data, and these are, for example, stored as a table in which a user health type is associated with a behavior expected to be performed by users corresponding to this type as shown in FIG. 14. When the user browses this in leaflet form, it is desirable for the content to be displayed as a photograph or a simplified cartoon as shown FIG. 9 so as to be easily understood.

(Step S1104)

In step S1104, the controller 205 operates as the document creation unit 307, and a story of the leaflet content to be presented to the user is determined for each type by a table in which the type classification result and a story of the leaflet content are associated with each other, registered as the data of the leaflet content stored in the storage unit 202.

The storage unit 202 stores this table, which is, for example, as shown in FIG. 15, data in which content of a corresponding story for each health type is associated with a brief explanation of that content.

(Step S1105)

In step S1105, the controller 205 operates as the document creation unit 307, and determines a face shot to be used for the leaflet for each type according to a table in which face shot data of a person connected to the user (e.g., a family member or a supervisor at work) is associated with the type classification result, registered as the leaflet content data stored in the storage unit 202.

Figure 16:
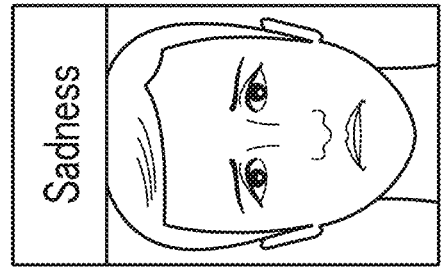
FIG. 16 is a diagram showing sample leaflet content DB for determining a face shot for each individual in step S1105 of FIG. 11.

The storage unit 202 stores a table in which this face shot data and a health type are associated with each other for each user. In this table, for example, as shown in FIG. 16, four types of facial expressions of expressionless, sadness, dislike, and anger are registered, and the face shot to be adopted is determined according to the health type. These face shots are, for example, displayed on the cover of the leaflet to impress the user. When the face shot data indicating four types of facial expressions do not exist in the storage unit 202, facial units are changed based on a stored face shot to create desired expression data. For example, the document creation unit 307 acquires the face shot data for "expressionless" from the storage unit 202, and when expressing sadness, changes such as lowering the outer corner of the eye, lowering the eyebrow, and lowering the corner of the mouth are performed on the face shot data to create face shot data for sadness. For other face shot data, the document creation unit 307 performs similar processing on the face shot data so as to obtain desired face shot data.

(Step S1106)

In step S1106, the controller 205 operates as the document creation unit 307, and determines a cover design to be used for the leaflet for each user type based on data in which cover design data of the leaflet and the type classification result are associated with each other, registered as the leaflet content data stored in the storage unit 202.

Figure 17:
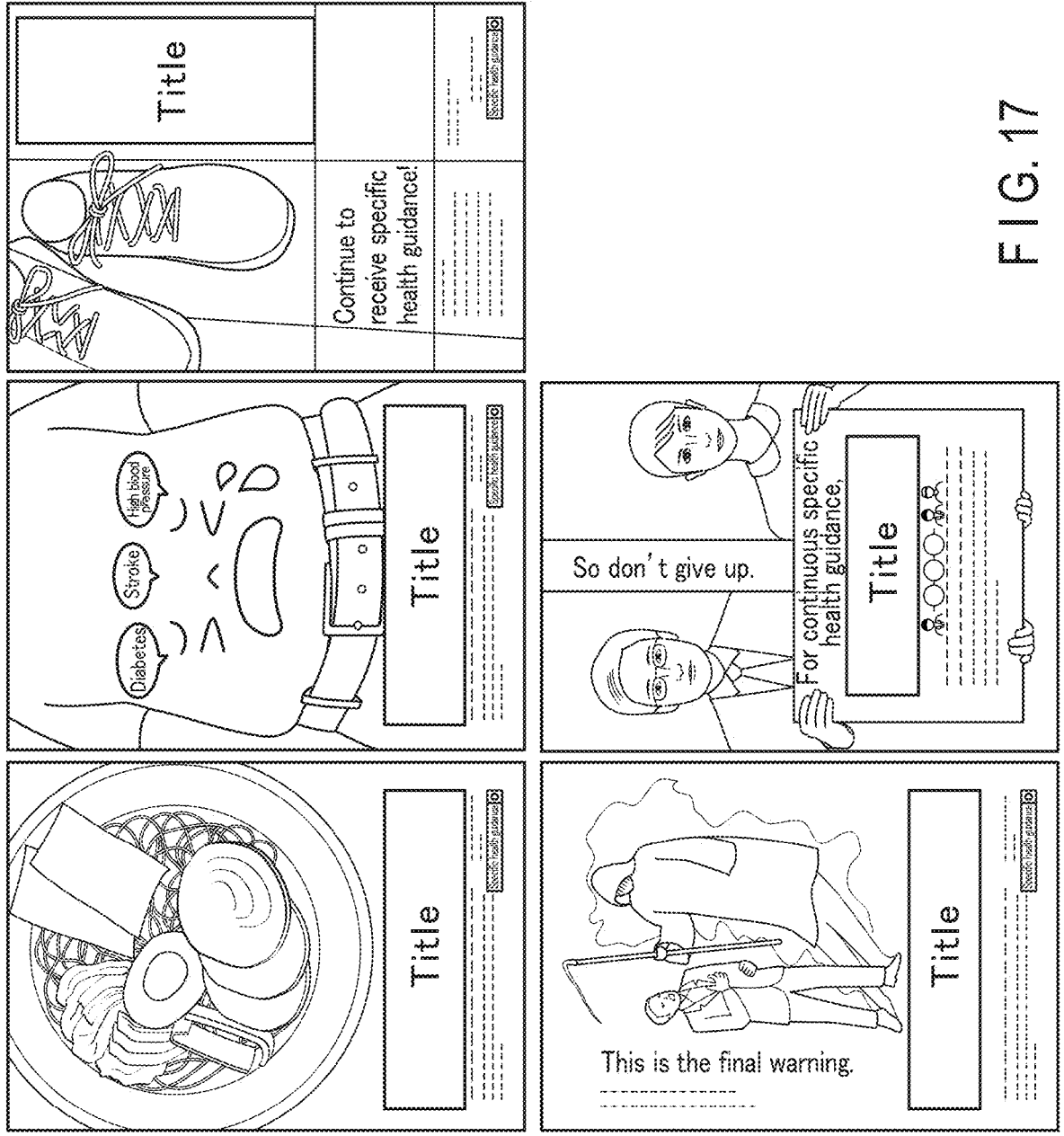
FIG. 17 is a diagram showing sample leaflet content DB for determining a cover design in step S1106 of FIG. 11.

The storage unit 202 stores at least one leaflet cover design template for each health type, and the document creation unit 307 adopts one template according to the determined health type. For example, the document creation unit 307 has leaflet cover design templates as shown in FIG. 17, acquires a corresponding template according to the determined health type, and applies the title determined in step S1101 to the template to create cover design data. If there exists other data necessary for the cover design, the document creation unit 307 embeds the data to create the cover data.

(Step S1107)

In step S1107, the controller 205 operates as the document creation unit 307, and creates leaflet data (document data) by integrating the title data, feedback data of a health checkup result, presentation data of expected behavior, story data, face shot data for each user, and cover design data, which are units of the leaflet determined from step S1101 to step S1106.

The document creation unit 307 creates the document data to form a leaflet (document) as shown in FIG. 18 by using the parts data of the leaflet determined in the above steps. This step completes the leaflet data, including the leaflet to be presented to the user.

Next, with reference to FIG. 19, a description will be given of a method for determining a type without increasing the number of classifications (i.e., the number of types) when the type determination unit 305 determines a health type of a user in a case where the type determination unit 305 inputs a large number of data types. In the present embodiment, the health checkup data and at least one of the health consciousness data, environment data, or knowledge data are input. However, as described above, each of these four pieces of data may include a plurality of pieces of data, and thus the number of types of data may be larger than four. Therefore, in general, when the number of types of input data related to a user is n (n is a natural number), the type determination unit 305 determines a health type of the user using an n-dimensional space. The health type of the user can be determined according to a position determined by data of the user distributed in the n-dimensional space.

Figure 19:
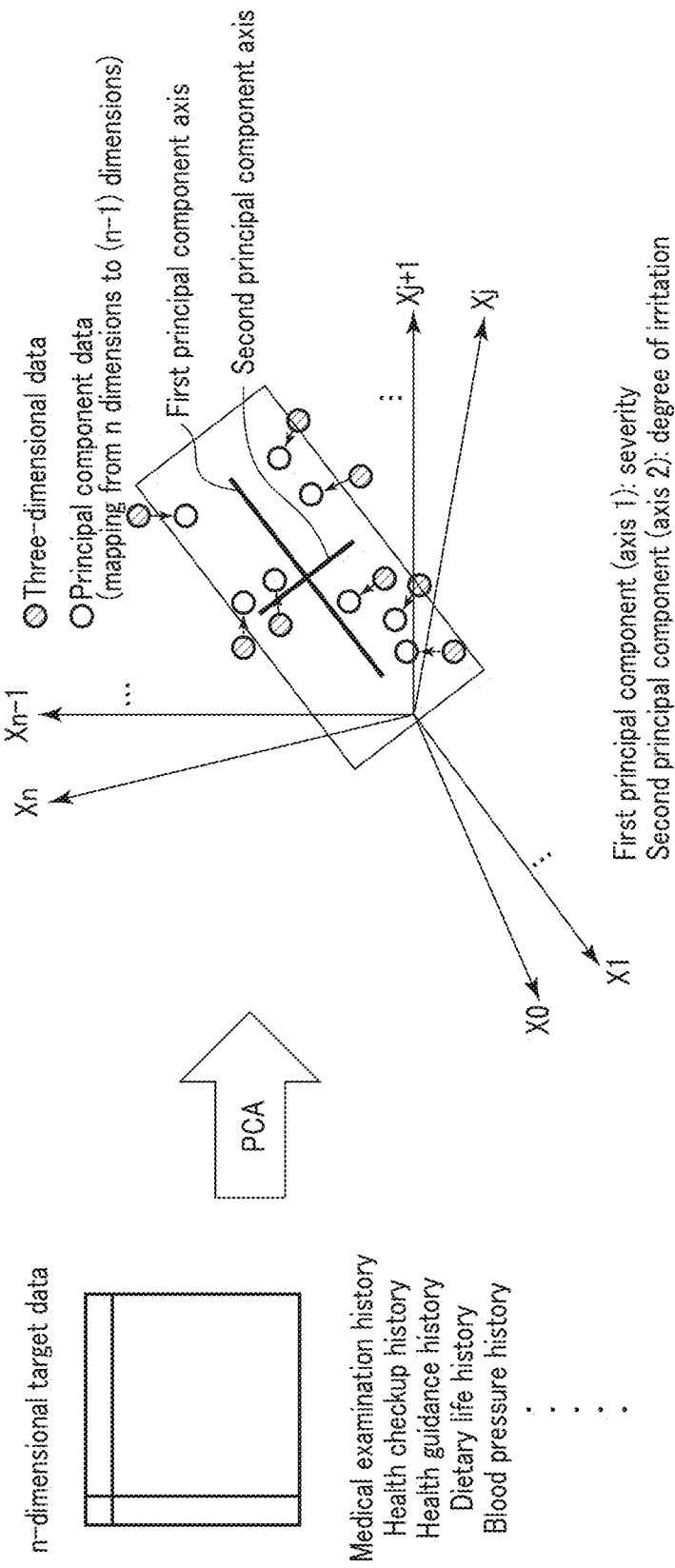
FIG. 19 is a diagram showing an example of a concept of a principal component analysis that can be performed by a type determination unit of FIG. 3.

In FIG. 19, in a case where the type determination unit 305 handles n-dimensional data of many users, it is possible to apply a principal component analysis (PCA) by using these many pieces of data to compress the dimension of the n-dimensional space (also referred to as "dimensionality reduction"), and select a new axis serving, as a principal component of this data. In the example shown in FIG. 19, the dimensionality compression is repeated from the n-dimensional space, and the type classification is made possible by the two new axes of the first principal component and the second principal component. Thus, a health type of a user can be determined with a small number of types using the characteristic principal components of these data as axes. If the dimension is compressed to two axes, the health type can be determined in the same manner as the classification in the two-dimensional space described above.

In the example shown in FIG. 19, as the n-dimensional data, the above-described medical data, health guidance data, health checkup data, environment-related question and answer data, and health knowledge data are adopted. Specifically, as the n-dimensional data, data included in these data, e.g., medical examination presence/absence data indicating presence/absence of reception of a medical examination, health checkup data, health guidance presence/absence data, dietary data, blood pressure value data, etc. among the medical data may be adopted. The classification by these plurality of data items in the n-dimensional space has a large dimension and an enormous number of health type classifications. However, by applying the principal component analysis to these data, the number of health type classifications can be reduced by aggregating information into a dimension smaller than the n-dimension. Since the number of type classifications can be reduced, it is possible to prevent the number of document data types according to the type from becoming enormous, and a more appropriate number of document data types can be set. Furthermore, in this method, since a plurality of data items are projected from the n-dimensional space to a space spanned by principal component vectors, useful data characteristics are selected from the data in the original n-dimensional space, and the most effective health type can be set.

Next, with reference to FIGS. 20 and 21, a description will be given for changing a display design of a document such as a leaflet according to a health type of a user to select an optimum display desk n for the user of that type.

The document creation unit 307 creates document data according to a health type in order to make a user interested in the content of the leaflet so as to be aware of their own health condition by the health type, and stimulate the user with the means for achieving an objective therefor and the confidence to firmly believe in achievement of the objective. Specifically, the content and design of the leaflet are changed according to the health type. For example, a title, feedback of a health checkup result, presentation of expected user behavior, a future story, etc. are changed to those suitable for the user health type. These changes are realized by, for example, a framework organized into three factors of "Attention", "Relevance", and "Confidence" shown in FIG. 20, a motivating means corresponding to each factor, a procedure for designing a motivation, etc.

Next, how the design of the leaflet is changed depending on the health type will be described with reference to FIG. 21.

In addition to the title and content changed according to the health type as shown in FIG. 8, the design is changed according to the health type as shown in the right end of FIG. 21. In the example of FIG. 21, since health types (5) and (3) have an actual result of undergoing a medical examination or health guidance, importance is placed on relevance rather than attention, and the design is changed to a design for impressing the factor of "relevance" upon the user so that they feel the lifestyle disease to be their own problem, and not someone else's. In the health types (4), (2), and (1), since there is no actual result of undergoing a medical examination or receiving health guidance, the design is changed to one which impresses the factor of "attention" upon the user so that they read the document in the first place. In addition, in any health type, a design for presenting a behavior that can be immediately carried out to the user and impressing the factor of "self-confidence" upon the user in order to create a sense of achievement that their own behavior can be controlled is adopted.

Next, the setting of a condition for notifying a user of a document as an item to be changed according to health type will be described with reference to FIG. 22.

Five health types are classified as shown in FIG. 8 according to the input data of sense of crisis and severity, and a notification time, a notification distance, and a notification frequency are set as shown in FIG. 22 as conditions for notifying the user of the document according to the health types.

The notification time is a time at which the document data is notified to the user, and includes, for example, "when health checkup result is notified" and "before health guidance application deadline". In the example of FIG. 22, there are two categories depending on whether the user undergoes a medical examination or receives health. guidance. A user who does not undergo a medical examination or receive health guidance is notified of a document. "before health guidance application deadline", which is a different point from other users.

The notification distance is for transmitting the document data to the user when a distance between a location of a medical institution and/or a health care institution and the user is within a set distance. This location information may be set either by the user or a medical institution and/or a health care institution at the time of health checkup. The distance may be measured by any method, but is preferably measured automatically, for example, by using a GPS function of a user's portable information terminal (e.g., a smartphone). In the example, of FIG. 22, it is set so that the notification is given to a more severely ill user even if they are distant from a medical institution and/or a health care institution.

The notification frequency is a frequency of transmitting the document data to the user, and is, for example, a frequency of transmitting the document data. within a predetermined period (e.g., one day) when the document data is transmitted based on the notification time and the notification distance. In the example of FIG. 22, the notification frequency to a user who does not undergo a medical examination or receive health guidance is set to be higher than that of other users, and, for example, in the case of health type (4), transmission is set to be performed twice within a predetermined period.

Next, with reference to FIG. 23, a description will be given of a case where the face shot data acquired by the document creation unit 307 from the storage unit 202 is adopted as a face shot of a person on a cover, etc. of a leaflet.

Figure 23:
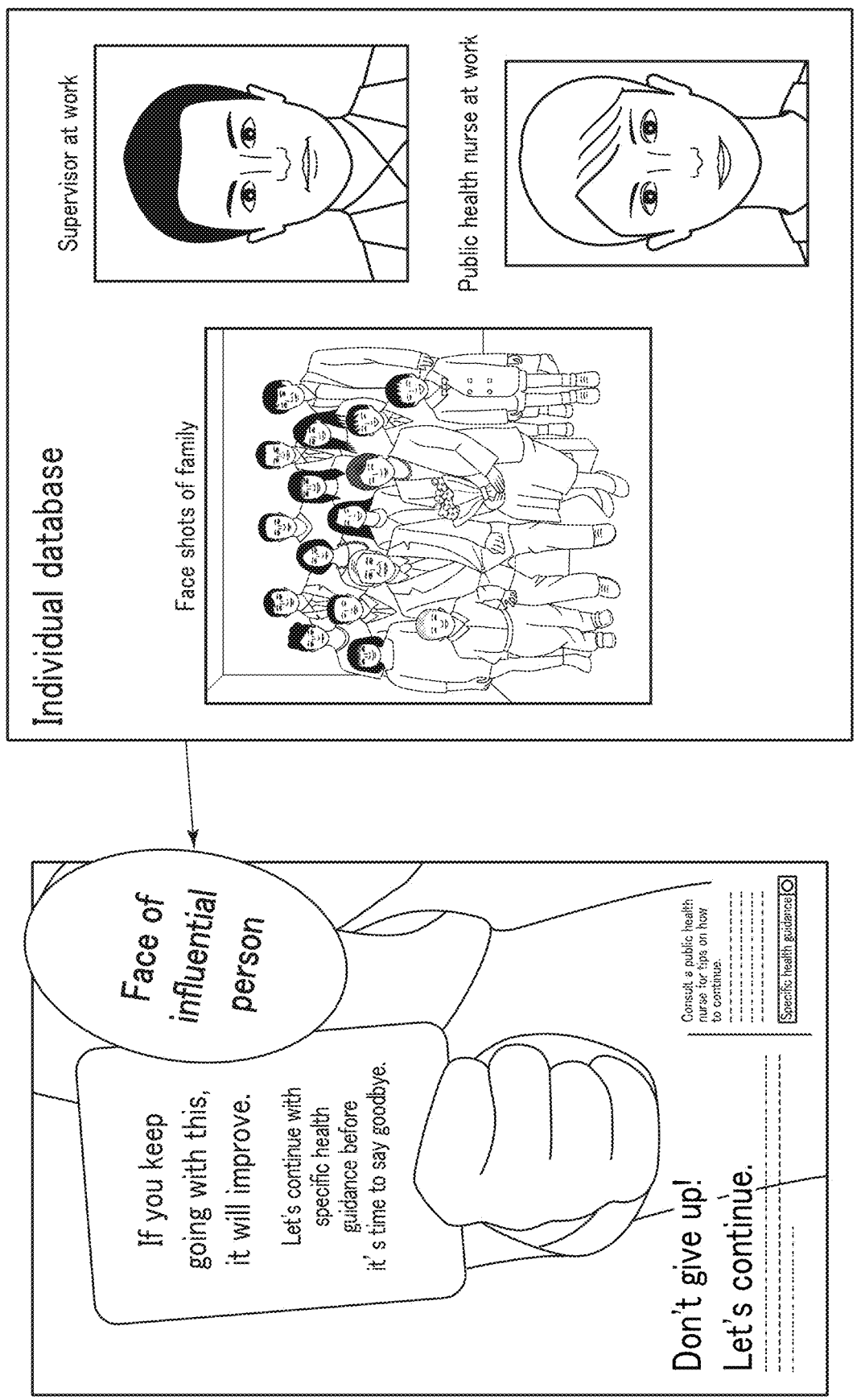
FIG. 23 is a diagram showing a concept in which the document creation unit of FIG. 3 selects a face shot of a person having an influence on the user.

As shown in FIG. 23, face shot data of people connected to a user individual are stored in the storage unit 202. These face shot data include, for example, a face shot of a family member, a photograph of a supervisor at work, and a photograph of a public health nurse. These photograph data are face shots which are considered to have an influence on the user, and the photograph to be posted may be changed depending on the content of the document to be adopted. By setting the kind of document content for which each photograph is used, an optimal face shot can be posted, and a psychological impression given to the user can be strengthened. For example, it is conceivable that in a case of a document including strong advice to a user, a photograph of a supervisor at work may be associated with the content; in a case of content recommending the user receive health guidance, a photograph of a public health nurse at work may be associated; and in a case of document content related to daily life such as a user's lifestyle disease, a face shot of a family member may be associated.

[Operation and Effect]

As described above, in steps S401, S402, S403, and S404, the document creation apparatus 101 according to the present embodiment acquires any one of the user's health consciousness data, environment-related question and answer data, and health knowledge data, and the health checkup data. The health consciousness data includes, for example, data indicating whether or not a medical examination has been undergone and/or health guidance received. In step S406, the type determination unit 305 of the document creation apparatus 101 determines the health type of the user based on the data acquired in steps S401 to S404. Therefore, the document creation apparatus 101 can accurately determine the health type of the user based on the user health checkup data and other data on health unique to the user. Next, document data to be presented to the user is created according to the health type determined in step S406. In the case of creating the document data, the type determination unit 305 acquires face shot data of a person connected to the user from the storage unit 202, and appropriately arranges the face shot data at an appropriate place in the document according to the type of influence on the user. The type determination unit 305 can also acquire title data, document design data, user feedback data, and story data from the leaflet content data stored in the storage unit 202, and create the document data from these data. Therefore, according to the document creation apparatus 101 of the present embodiment, it is possible to create a document to effectively make a user aware of their health condition. Further, according to the document creation apparatus 101, it is possible to create a document to effectively make the user aware that they should actively receive health guidance and/or undergo a medical examination.

[Modifications]

While the embodiments of the present invention have been described in detail, the foregoing descriptions are merely illustrative of the present invention in every respect. Needless to say, various improvements and modifications can be made without departing from the scope of the invention. For example, the modifications set forth below are possible. Further, in implementing the present invention, a specific configuration according to the embodiment may be appropriately adopted. In the following descriptions, the same components as those in the above-described embodiment are denoted by the same reference numerals, and descriptions of the same points as those in the above-described embodiment are omitted as appropriate. The following modifications can be appropriately combined.

<1>

The smartphone 131 or the computer 132 may store a program incorporated into the document creation apparatus 101, acquire at least one of the health consciousness data, environment-related question and answer data, or health knowledge data, and the health checkup data directly from the medical server 111 or the insurance society server 112 or via the document creation apparatus 101, and create document data using the program.

<2>

The apparatus of the present invention can also be realized by a computer and a program, and the program can be recorded in a recording medium (or a storage medium) or provided through a network.

Each of the above-described devices and device portions can be implemented by either a hardware configuration or a configuration in which hardware resources and software are combined. As the software of the combination configuration, a program is used which is installed in a computer from a network or a computer-readable recording medium (or storage medium) in advance. and is executed by a processor of the computer to cause the computer to realize an operation (or function) of each device.

<3>

It should be noted that the present invention is not limited to the above-described embodiment as is, but can be embodied by modifying elements without departing from the scope of the invention in an implementation stage. In addition, various inventions can be formed by appropriately combining a plurality of elements disclosed in the above embodiment. For example, some elements may be deleted from all the elements indicated in the embodiment. Furthermore, elements of different embodiments may be appropriately combined.

In addition, "and/or" means any one or more of items listed with "and/or". As a specific example, "x and/or y" means any element of a set {(x), (y), (x, y)}consisting of three elements. As another specific example, "x, y, and/or z" means any element of a set of seven elements {(x), (y), (z), (x, y), (x, z), (y, z), (x, y, z)}.

(Supplemental Note 1)

A document creation apparatus (101) comprising a first acquisition unit (301) that acquires health data indicating a health condition of a user, a second acquisition unit (302, 303, 304) that acquires at least one of consciousness data indicating health consciousness of the user, environment data indicating an environment related to health of the user, or knowledge data indicating a knowledge level related to the health of the user, a determination unit (305) that determines a type related to the health of the user based on a position of a point corresponding to the data acquired by the first acquisition unit and the second acquisition unit in a space spanned by at least one vector among one or more vectors having consciousness data as a value, one or more vectors having the environment data as a value, or one or more vectors having the knowledge data as a value, and one or more vectors having the health data as a value, and a creation unit (307) that creates document data for a document to be presented to the user according to the type.

REFERENCE SIGNS LIST

101 . . . document creation apparatus
111 . . . medical server
112 . . . insurance society server
121 . . . network
131 . . . smartphone
132 . . . computer
201 . . . communication interface
202 . . . storage unit
203 . . . input device
204 . . . output device
205 . . . controller
206 . . . timing device
207 . . . power supply unit
208 . . . drive
209 . . . external interface
301 . . . health data acquisition unit
302 . . . consciousness data acquisition unit
303 . . . environment data acquisition unit
304 . . . knowledge data acquisition unit
305 . . . type determination unit
306 . . . priority determination unit
307 . . . document creation unit
308 . . . transmission unit

The invention claimed is:

1. A document creation apparatus comprising a processor configured with a program to perform operations comprising:

operation as a first acquisition unit configured to acquire first data comprising one or more elements of health data indicating a health condition of a user;

operation as a second acquisition unit configured to acquire second data comprising: at least one of: one or more elements of consciousness data indicating health consciousness of the user, one or more elements of environment data indicating an environment related to health of the user, or one or more elements of knowledge data indicating a knowledge level related to the health of the user;

operation as a determination unit configured to determine a type of the health of the user based on a position of a point corresponding to the one or more elements of the first data acquired by the first acquisition unit and the one or more elements of the second data acquired by the second acquisition unit in a space spanned by one or more bases, the one or more bases being one or more vectors having the health data as a value, and at least one vector of one or more vectors having the consciousness data as a value, one or more vectors having the environment data as a value, or one or more vectors having the knowledge data as a value;

operation as a creation unit configured to create document data for creating a document to be presented to the user according to the determined type;

operation as a priority determination unit configured to determine elements of data to adopt, the elements of the data comprising the one or more elements of the first data and the one or more elements of the second data, by comparing content of the elements of data with a limit of an amount of content to be included in the document and a threshold value of a priority to be set for the elements of the data and adopting elements of data that do not exceed the limit of an amount of content, and higher than the threshold value of the priority; and operation as a generation unit configured to generate a new space in which a number of dimensions is reduced using a principal component analysis from a dimensional space having a number of dimensions corresponding to a number of the vectors, such that operation as the determination unit comprises determining the type based on one or more principal component vectors of the new space, wherein operation as the priority determination unit comprises determining elements of data to adopt for presentation to the user comprising the elements of data that do not exceed the limit of an amount of content, and having the priority higher than the threshold value of the priority and arranging the elements of data in a descending order of priority beginning from elements of first data included in the health data, and operation as the creation unit comprises creating the document data for a document to be presented to the user with the adopted elements of data.

2. The document creation apparatus according to claim 1, wherein the determination unit is configured to:
calculate a severity of the health condition of the user from the health data, and calculate a sense of crisis of the user from the consciousness data; and
determine the type based on at least one of the calculated severity of the health condition or the calculated sense of crisis.

3. The document creation apparatus according to claim 1, wherein
operation as the determination unit comprises determining whether to encourage the user to undergo a doctor's medical examination, recommending the user to receive health guidance, or neither encouraging the user nor recommending the user, according to the type, and
operation as the creation unit comprises creating the document data including content changed according to a result of the determination.

4. The document creation apparatus according to claim 1, wherein operation as the determination unit comprises digitizing the consciousness data according to an answer from the user to a question about the health consciousness of the user, digitizing the environment data according to an answer from the user to at least one of questions about diet of the user, exercise of the user, sleep of the user, a family medical history, or a smoking status of people around the user, and digitizing the knowledge data according to an answer from the user to a question about knowledge related to the health of the user.

5. The document creation apparatus according to claim 1, wherein operation as the creation unit comprises creating at least one data of title data indicating a title of the document, feedback data to the user for a health checkup result included in the health data of the user, behavior data indicating a behavior expected of the user corresponding to the type, story data indicating a story according to at least one of an advantage and a disadvantage indicated by the behavior data, expression data indicating an expression according to the type and included in the environment data, design data indicating an arrangement of content of the document, layout data of content included in the document according to the type, or image data of a diagram and a photograph, content of the title data, the feedback data, the behavior data, the story data, the expression data, the design data, and the layout data being changed per the type, and using the created data as content included in the document.

6. The document creation apparatus according to claim 5, wherein operation as the creation unit comprises creating the title data, the feedback data, the behavior data, the story data, the expression data, and the design data according to at least one of the type or the knowledge data.

7. The document creation apparatus according to claim 5, wherein operation as the creation unit comprises creating, as the feedback data, data including a display format and a text corresponding to the type of the user.

8. The document creation apparatus according to claim 5, wherein operation as the creation unit comprises:
creating, as the story data, a story representing an advantage included in the behavior data, or create a story representing a disadvantage when the type includes content triggered by a bad user habit; and
creating, according to the type, data including layout data of content included in the document data and image data of a diagram and a photograph.

9. The document creation apparatus according to claim 5, wherein
operation as the second acquisition unit comprises acquiring portrait data of a person connected to the user, and
operation as the creation unit comprises creating the expression data using the portrait data.

10. The document creation apparatus according to claim 1, wherein the processor is configured with the program to perform operations further comprising operation as a transmission unit configured to transmit the document data to a terminal capable of receiving the document data and displaying the document.

11. The document creation apparatus according to claim 1, wherein the processor is configured with the program to perform operations further comprising operation as a presentation unit configured to present content represented by the document data to the user.

12. A document creation method comprising:
acquiring first data comprising one or more elements of health data indicating a health condition of a user;
acquiring second data comprising: at least one of: one or more elements of consciousness data indicating health consciousness of the user, one or more elements of environment data indicating an environment related to health of the user, or one or more elements of knowledge data indicating a knowledge level related to the health of the user;
determining a type related to the health of the user based on a position of a point corresponding to the one or more elements of the first acquired data and the one or more elements of the second acquired data in a space spanned by one or more bases, the one or more bases being one or more vectors having the health data as a value, and at least one vector of one or more vectors having the consciousness data as a value, one or more vectors having the environment data as a value, or one or more vectors having the knowledge data as a value;
creating document data to be presented to the user according to the type;
determining elements of data to adopt, the elements of the data comprising the one or more elements of the first data and the one or more elements of the second data, by comparing content of the elements of data with a limit of an amount of content to be included in the document and a threshold value of a priority to be set for the elements of the data and adopting elements of data that do not exceed the limit of an amount of content, and meet or exceed the threshold value of the priority; and generating a new space in which a number of dimensions is reduced using a principal component analysis from a dimensional space having a number of dimensions corresponding to a number of the vectors, such that determining a type related to the health of the user comprises determining the type based on one or more principal component vectors of the new space, wherein creating the document data comprises creating the document data for a document to be presented to the user with the adopted data.

13. A non-transitory computer readable medium storing a computer program, which, when executed by a computer, performs operations comprising:

acquiring first data comprising one or more elements of health data indicating a health condition of a user;

acquiring second data comprising: at least one of: one or more elements of consciousness data indicating health consciousness of the user, one or more elements of environment data indicating an environment related to health of the user, or one or more elements of knowledge data indicating a knowledge level related to the health of the user;

determining a type related to the health of the user based on a position of a point corresponding to the one or more elements of the first acquired data and the one or more elements of the second acquired data in a space spanned by one or more bases, the one or more bases being one or more vectors having the health data as a value, and at least one vector of one or more vectors having the consciousness data as a value, one or more vectors having the environment data as a value, or one or more vectors having the knowledge data as a value;

creating document data to be presented to the user according to the type;

determining elements of data to adopt, the elements of the data comprising the one or more elements of the first data and the one or more elements of the second data, by comparing content of the elements of data with a limit of an amount of content to be included in the document and a threshold value of a priority to be set for elements of the data and adopting elements of data that do not exceed the limit of an amount of content, and meet or exceed the threshold value of the priority; and generating a new space in which a number of dimensions is reduced using a principal component analysis from a dimensional space having a number of dimensions corresponding to a number of the vectors, such that determining a type related to the health of the user comprises determining the type based on one or more principal component vectors of the new space, wherein creating the document data comprises creating the document data for a document to be presented to the user with the adopted data.

14. The document creation apparatus according to claim 6, wherein operation as the creation unit comprises creating, as the feedback data, data including a display format and a text corresponding to the type of the user.

15. The document creation apparatus according to claim 6, wherein operation as the creation unit comprises:

creating, as the story data, a story representing an advantage included in the behavior data, or create a story representing a disadvantage when the type includes content triggered by a bad user habit; and creating, according to the type, data including layout data of content included in the document data and image data of a diagram and a photograph.

16. The document creation apparatus according to claim 6, wherein operation as the second acquisition unit comprises acquiring portrait data of a person connected to the user, and operation as the creation unit comprises creating the expression data using the portrait data.

17. The document creation apparatus according to claim 2, wherein the processor is configured with the program to perform operations further comprising operation as a transmission unit configured to transmit the document data to a terminal capable of receiving the document data and displaying the document.

18. The document creation apparatus according to claim 2, wherein the processor is configured with the program to perform operations further comprising operation as a presentation unit configured to present content represented by the document data to the user.

* * * * *